US011116739B2

(12) United States Patent
Newton et al.

(10) Patent No.: US 11,116,739 B2
(45) Date of Patent: Sep. 14, 2021

(54) FIXED DOSE COMBINATIONS AND FORMULATIONS COMPRISING ETC1002 AND ONE OR MORE STATINS AND METHODS OF TREATING OR REDUCING CARDIOVASCULAR DISEASE

(71) Applicant: Esperion Therapeutics, Inc., Ann Arbor, MI (US)

(72) Inventors: Roger Schofield Newton, Ann Arbor, MI (US); Noah Laban Rosenberg, Livingston, NJ (US); Diane Elaine MacDougall, Lincoln, MA (US)

( * ) Notice: Subject to any disclaimer, the term of this patent is extended or adjusted under 35 U.S.C. 154(b) by 0 days.

(21) Appl. No.: 15/558,519

(22) PCT Filed: Mar. 16, 2016

(86) PCT No.: PCT/US2016/022694
§ 371 (c)(1),
(2) Date: Sep. 14, 2017

(87) PCT Pub. No.: WO2016/149405
PCT Pub. Date: Sep. 22, 2016

(65) Prior Publication Data
US 2018/0078518 A1    Mar. 22, 2018

Related U.S. Application Data

(60) Provisional application No. 62/133,739, filed on Mar. 16, 2015, provisional application No. 62/277,403, filed on Jan. 11, 2016.

(51) Int. Cl.
| | |
|---|---|
| *A61K 31/20* | (2006.01) |
| *A61K 31/22* | (2006.01) |
| *A61K 31/366* | (2006.01) |
| *A61K 31/40* | (2006.01) |
| *A61K 31/405* | (2006.01) |
| *A61K 31/47* | (2006.01) |
| *A61K 31/505* | (2006.01) |

(52) U.S. Cl.
CPC .............. *A61K 31/20* (2013.01); *A61K 31/22* (2013.01); *A61K 31/366* (2013.01); *A61K 31/40* (2013.01); *A61K 31/405* (2013.01); *A61K 31/47* (2013.01); *A61K 31/505* (2013.01)

(58) Field of Classification Search
CPC ...... A61K 31/20; A61K 31/22; A61K 31/366; A61K 31/40; A61K 31/405; A61K 31/47; A61K 31/505
See application file for complete search history.

(56) References Cited

U.S. PATENT DOCUMENTS

| | | |
|---|---|---|
| 3,152,148 A | 10/1964 | Easterly et al. |
| 3,441,605 A | 4/1969 | Blake |
| 3,773,946 A | 11/1973 | Creger |
| 3,930,024 A | 12/1975 | Creger |
| 4,281,200 A | 7/1981 | Snoble |
| 4,287,200 A | 9/1981 | Kawamatsu et al. |
| 4,584,321 A | 4/1986 | Manghisi et al. |
| 4,613,593 A | 9/1986 | Yamatsu et al. |
| 4,634,119 A | 1/1987 | Pesthy |
| 4,634,719 A | 1/1987 | Takaishi et al. |
| 4,639,344 A | 1/1987 | Ueno et al. |
| 4,689,344 A | 8/1987 | Bar-Tana |
| 4,711,896 A | 12/1987 | Bar-Tana et al. |
| 4,714,762 A | 12/1987 | Hoefle et al. |
| 4,896,344 A | 1/1990 | Grady et al. |
| 5,166,174 A | 11/1992 | Ueno et al. |
| 5,225,439 A | 7/1993 | Ueno et al. |
| 5,284,858 A | 2/1994 | Ueno et al. |
| 5,380,709 A | 1/1995 | Ueno et al. |
| 5,428,062 A | 6/1995 | Ueno et al. |
| 5,502,198 A | 3/1996 | Picard et al. |
| 5,504,073 A | 4/1996 | Homan |
| 5,570,569 A | 11/1996 | Masuda |
| 5,578,639 A | 11/1996 | Homan |
| 5,633,287 A | 5/1997 | Lee et al. |
| 5,648,387 A | 7/1997 | Bisgaier et al. |
| 5,750,569 A | 5/1998 | Bisgaier et al. |
| 5,756,344 A | 5/1998 | Onda et al. |
| 5,756,544 A | 5/1998 | Bisgaier et al. |
| 5,783,600 A | 7/1998 | Bisgaier et al. |
| 5,834,596 A | 11/1998 | Ageland et al. |
| 5,886,034 A | 3/1999 | Ueno et al. |

(Continued)

FOREIGN PATENT DOCUMENTS

| | | |
|---|---|---|
| CN | 107530308 A | 1/2018 |
| EP | 0284108 A2 | 9/1988 |

(Continued)

OTHER PUBLICATIONS

Evaluation of ETC-1002 vs Placebo in Patients Receiving Ongoing Statin Therapy, Clinical Trial NCT02072161 first posted Feb. 26, 2014.*
Gray et al., Current Medical Research and Opinion, vol. 26, No. 3, 2010, 537-547.*
Masuda et al., "Ezetimibe Improves Postprandial Hyperlipidaemia in Patients with Type IIb Hyperlipidaemia," Eur. J. Clin. Invest., vol. 39 (8), 2009, pp. 689-698.
Akdim et al., "Efficacy and Safety of Mipomersen, an Antisense Inhibitor of Apolipoprotein B, in Hypercholesterolemic Subjects Receiving Stable Statin Therapy," J. Am. Coll. Cardiol., vol. 55, Apr. 13, 2010, pp. 1611-1618.
Norata et al., "New Therapeutic Principles in Dyslipidaemia: Focus on LDL and Lp(a) Lowering Drugs," Eur. Heart J., vol. 34(24); Mar. 18, 2013, pp. 1783-1789a.

(Continued)

*Primary Examiner* — Jared Barsky
(74) *Attorney, Agent, or Firm* — Goodwin Procter LLP

(57) ABSTRACT

Disclosed herein are compositions comprising fixed doses of ETC-1002 and one or more statins. Also disclosed herein are methods for using fixed doses of ETC-1002 and one or more statins. Uses include methods of treating cardiovascular disease or reducing the risk of cardiovascular disease in a subject. Uses also include methods of treating hypercholesterolemia in a subject.

1 Claim, 2 Drawing Sheets

(56) References Cited

U.S. PATENT DOCUMENTS

| | | | |
|---|---|---|---|
| 5,968,963 A | 10/1999 | Homan | |
| 5,981,595 A | 11/1999 | Picard et al. | |
| 6,004,925 A | 12/1999 | Dasseux et al. | |
| 6,017,905 A | 1/2000 | Roark et al. | |
| 6,037,323 A | 3/2000 | Dasseux et al. | |
| 6,093,719 A | 7/2000 | Bocan | |
| 6,093,744 A | 7/2000 | Lee et al. | |
| 6,124,309 A | 9/2000 | Bocan | |
| 6,143,755 A | 11/2000 | Bocan | |
| 6,207,822 B1 | 3/2001 | Thiruvengadam et al. | |
| 6,362,236 B1 | 3/2002 | Aviram et al. | |
| RE37,721 E | 5/2002 | Rosenblum et al. | |
| 6,410,802 B1 | 6/2002 | Dasseux et al. | |
| 6,459,003 B1 | 10/2002 | Dasseux et al. | |
| 6,506,799 B1 | 1/2003 | Dasseux | |
| 6,646,170 B2 | 11/2003 | Dasseux et al. | |
| 6,673,780 B2 | 1/2004 | Dasseux et al. | |
| 6,699,910 B2 | 3/2004 | Dasseux et al. | |
| 6,703,422 B2 | 3/2004 | Dasseux et al. | |
| 6,713,507 B2 | 3/2004 | Dasseux et al. | |
| 6,790,953 B2 | 9/2004 | Dasseux et al. | |
| 6,831,105 B2 | 12/2004 | Dasseux | |
| 6,909,014 B2 | 6/2005 | Dasseux et al. | |
| 7,053,080 B2 | 5/2006 | Davis et al. | |
| 7,119,221 B2 | 10/2006 | Dasseux et al. | |
| 7,192,940 B2 | 3/2007 | Dasseux et al. | |
| 7,304,093 B2 | 12/2007 | Dasseux et al. | |
| 7,335,799 B2 | 2/2008 | Dasseux et al. | |
| 7,405,226 B2 | 7/2008 | Dasseux et al. | |
| 7,576,130 B2 | 8/2009 | Dasseux et al. | |
| 7,705,177 B2 | 4/2010 | Oniciu et al. | |
| 7,812,199 B2 | 10/2010 | Dasseux et al. | |
| 7,838,554 B2 | 11/2010 | Dasseux et al. | |
| RE42,461 E | 6/2011 | Rosenblum et al. | |
| 8,067,466 B2 | 11/2011 | Dasseux et al. | |
| 8,084,498 B2 | 12/2011 | Dasseux et al. | |
| 8,153,690 B2 | 4/2012 | Dasseux et al. | |
| 8,309,604 B2 | 11/2012 | Dasseux et al. | |
| 8,497,301 B2 | 7/2013 | Dasseux et al. | |
| 8,623,915 B2 | 1/2014 | Dasseux et al. | |
| 8,642,653 B2 | 2/2014 | Dasseux et al. | |
| 8,975,300 B2 | 3/2015 | Dasseux et al. | |
| 9,000,041 B2 | 4/2015 | Dasseux et al. | |
| 9,006,290 B2 | 4/2015 | Dasseux et al. | |
| 9,452,964 B2 | 9/2016 | Dasseux et al. | |
| 9,624,152 B2 | 4/2017 | Dasseux et al. | |
| 10,047,028 B2 | 8/2018 | Dasseux et al. | |
| 10,118,881 B2 | 11/2018 | Dasseux et al. | |
| 2003/0180352 A1 | 9/2003 | Patel et al. | |
| 2004/0214777 A1 | 10/2004 | McGrath | |
| 2004/0214887 A1 | 10/2004 | Dasseux et al. | |
| 2005/0043278 A1 | 2/2005 | Dasseux et al. | |
| 2005/0119333 A1 | 6/2005 | Dasseux | |
| 2005/0214887 A1 | 9/2005 | Emori et al. | |
| 2007/0155704 A1 | 7/2007 | Dasseux et al. | |
| 2007/0179120 A1 | 8/2007 | Dasseux et al. | |
| 2008/0249166 A1 | 10/2008 | Dasseux et al. | |
| 2009/0024789 A1 | 1/2009 | Rajan et al. | |
| 2009/0247489 A1 | 10/2009 | Dasseux et al. | |
| 2010/0234342 A1 | 9/2010 | Cifter et al. | |
| 2010/0291207 A1 | 11/2010 | Gat et al. | |
| 2010/0297105 A1 | 11/2010 | Geary et al. | |
| 2011/0262497 A1 | 10/2011 | Injac et al. | |
| 2012/0129930 A1 | 5/2012 | Dasseux et al. | |
| 2012/0135976 A1 | 5/2012 | Kerc et al. | |
| 2012/0225908 A1 | 9/2012 | Dasseux et al. | |
| 2013/0190354 A1 | 7/2013 | Wen et al. | |
| 2013/0280176 A1 | 10/2013 | Diezi et al. | |
| 2013/0302399 A1 | 11/2013 | Feldhaus et al. | |
| 2014/0093564 A1 | 4/2014 | Bradley et al. | |
| 2015/0005386 A1 | 1/2015 | Bisgaier | |
| 2015/0344388 A1 | 12/2015 | Dasseux et al. | |
| 2015/0344389 A1 | 12/2015 | Dasseux et al. | |
| 2017/0349516 A1 | 12/2017 | Dasseux et al. | |
| 2019/0084908 A1 | 3/2019 | Dasseux et al. | |

FOREIGN PATENT DOCUMENTS

| | | |
|---|---|---|
| EP | 0720599 A1 | 7/1996 |
| EP | 1047421 A2 | 11/2000 |
| EP | 1137634 A1 | 10/2001 |
| EP | 3270909 A1 | 1/2018 |
| FR | 1545224 A | 11/1968 |
| GB | 1196594 A | 7/1970 |
| GB | 1196595 A | 7/1970 |
| GB | 1196596 A | 7/1970 |
| GB | 1196598 A | 7/1970 |
| IN | 201717035904 | 12/2017 |
| MX | 262623 | 12/2008 |
| WO | WO-9630328 A1 | 10/1996 |
| WO | WO-9830530 A1 | 7/1998 |
| WO | WO-9900116 A2 | 1/1999 |
| WO | WO 99/26583 A2 | 6/1999 |
| WO | WO-2002030860 A2 | 4/2002 |
| WO | WO 2004/067489 A2 | 8/2004 |
| WO | WO 2005/062897 A2 | 7/2005 |
| WO | WO-2005068412 A1 | 7/2005 |
| WO | WO-2005109170 A2 | 11/2005 |
| WO | WO 07/058335 A1 | 5/2007 |
| WO | WO-2012040177 A1 | 3/2012 |
| WO | WO 2014/099584 A1 | 6/2014 |
| WO | WO 2016/149191 A1 | 9/2016 |
| WO | WO 2016/149405 A1 | 9/2016 |
| WO | WO-2017023165 A1 | 2/2017 |

OTHER PUBLICATIONS

Esperion Therapeutics, "Esperion Therapeutics Announces Positive Top-Line Phase 2b Results for ETC-1002, an Investigational Therapy for Patients With Hypercholesterolemia," Esperion Press Release, Oct. 1, 2014, entire document.

Int'l Search Report, PCT/US2016/022319, dated Jun. 3, 2016, 2 pages.

PCT Written Opinion, PCT Application No. PCT/US2016/022319, dated Jun. 3, 2016, 8 pages.

PCT International Search Report and Written Opinion, PCT Application No. PCT/US2016/022694, dated May 31, 2016, 12 pages.

United States Securities and Exchange Commission Form 10-Q, Esperion Therapeutics, Inc., Filed Nov. 6, 2013 for the Period Ending Sep. 30, 2013, 54 pages.

Berenson, A., "For Widely Used Drug, Question of Usefulness Is Still Lingering," The New York Times Company, Sep. 1, 2008, ©2018, 12 pages, [Online] [Retrieved Jan. 25, 2018] Retrieved from the Internet:<URL: http://www.nytimes.com/2008/09/02/business/02vytorin.html>.

Kolata, G., "Dashing Hopes, Study Shows a Cholesterol Drug Had No Effect on Heart Health," The New York Times Company, Apr. 3, 2016, ©2018, 9 pages, [Online] [Retrieved Jan. 25, 2018] Retrieved from the Internet:<URL: https://www.nytimes.com/2016/04/04/health/dashing-hopes-study-shows-cholesterol-drug-has-no-benefits.html>.

Asclepia Capital: Clarifying The Conversation Part II: Esperion Therapeutics, INc. (ESPR), Sep. 7, 2015, 9 pages.

Pinkosky, S.L. et al., "Liver-Specific ATP-Citrate Lyase Inhibition by Bempedoic Acid Decreases LDL-C and Attenuates Atherosclerosis," Nature Communications, Nov. 28, 2016, pp. 1-13.

U.S. Appl. No. 15/859,279, filed Dec. 29, 2017, Inventors: Mohamed Abdelnasser et al. [Copy Not Enclosed].

U.S. Appl. No. 62/456,571, filed Feb. 8, 2017, Inventors: Narendra Lalwani et al. [Copy Not Enclosed].

Pinkosky, S.L. et al., "AMP-Activated Protein Kinase and ATP-Citrate Lyase are Two Distinct Molecular Targets for ETC-1002, a Novel Small Molecule Regulator of Lipid and Carbohydrate Metabolism," Journal of Lipid Research, 2013, pp. 134-151, vol. 54.

Int'l Search Report, PCT/US2016/022694, dated May 31, 2016, 2 pages.

European Extended Search Report, European Application No. 16765550.5, dated Oct. 8, 2018, 8 pages.

Gagné, C. et al., "Efficacy and Safety of Ezetimibe Monotherapy in 6-10 Year Old Children with Heterozygous Familial or Nonfamilial

(56) References Cited

OTHER PUBLICATIONS

Hypercholesterolemia," Journal of Clinical Lipidology, Jan. 1, 2013, pp. 257-258, [Online] [Retrieved on Sep. 25, 2018] Retrieved from the Internet<URL:https://www.lipidjournal.com/article/S1933-2874(13)00108-6/pdf>.
Chilean Office Action, Chilean Application No. 2299-2017, dated Nov. 13, 2018, 12 pages.
Chilean Office Action, Chilean Application No. 2334-2017, dated Nov. 13, 2018, 15 pages.
European Extended Search Report, European Application No. 16765682.6, dated Jun. 28, 2018, 10 pages.
Anonymous: "NCT02072161: Evaluation of ETC-1002 vs Placebo in Patients Receiving Ongoing Statin Therapy," Clinicaltrials.gov, Apr. 3, 2014, pp. 1-9, [Online] [Retrieved on Jun. 20, 2018] Retrieved from the Internet<URL:https://clinicaltrials.gov/ct2/history/NCT02072161?V_2=View#StudyPageTop>.
Ballantyne, C. et al., "Abstract 17499: ETC-1002 Incrementally Lowers Low Density Lipoprotein-Cholesterol in Patients with Hypercholesterolemia Receiving Stable Statin Therapy," Circulation, Nov. 6, 2015, p. 1, vol. 132, No. Suppl. 3.
Ballantyne, C. et al., "Effect of ETC-1002 on Serum Low-Density Lipoprotein Cholesterol in Hypercholesterolemic Patients Receiving Statin Therapy," American Journal of Cardiology, Apr. 6, 2016, pp. 1928-1933, vol. 117, No. 12.
Ballantyne, C. et al., "Efficacy and Safety of a Novel Dual Modulator of Adenosine Triphosphate-Citrate Lyase and Adenosine Monophosphate-Activated Protein Kinase in Patients with Hypercholesterolemia," Journal of the American College of Cardiology, Sep. 24, 2013, pp. 1154-1162, vol. 62, No. 13.
Gutierrez, M. J. et al., "Efficacy and Safety of ETC-1002, a Novel Investigational Low-Density Lipoprotein-Cholesterol-Lowering Therapy for the Treatment of Patients with Hypercholesterolemia and Type 2 Diabetes Mellitus," Arteriosclerosis Thrombosis and Vascular Biology, Mar. 2014, pp. 676-683, vol. 34, No. 3.
Nikolic, D. et al., "ETC-1002: A Future Option for Lipid Disorders?" Atherosclerosis, Elsevier, Dec. 2014, pp. 705-710, vol. 237, No. 2.
Ackerly, et al., 1995, "A novel approach to dual-acting thromboxane receptor antagonist/synthase inhibitors based on the link of 1.3-dioxane-thromboxane receptor antagonists and -thromboxane synthase inhibitors", J. Med. Chem. 38:1608-1628.
Acton, et al., 1996, "Identification of scavenger receptor SR-B1 as high density lipoprotein receptor", Science. 271(5248):518-20.
Zahid Ahmad "Statin Intolerance" The American Journal of Cardiology, May 15, 2014, 1765-1771.
Ahrens, et al., 1967, "A direct method for preparing pyridoxal and 4-pyridoxic acid (1)", J. Heterocyl. Chem. 4:625-26.
Alexander, K., et al., 1948, "4.4-Dichlorodibutyl ether and its derivatives from tetrahydrofuran", J. Am. Chem. Soc. 70:1839-42.
Ansels, Pharmaceutical Dosage Forms and Drug Delivery Systems, 7th Ed. 1999, Lippincott, Williams and Wilkins; Chapters 3 and 7; pp. 60-100 and 179-228.
Aulton et al., Aulton's Pharmaceutics: The Design and Manufacture of Medicines, 4th Edition, Edited by Michael E. Aulton and Kevin M.G. Taylor, 2013, Churchill Livingstone Elsevier, Chapter 12.
Badimon, et al., 1992, "Role of High density lipoproteins in the regression of atherosclerosis", Circulation 85 (Suppl);11186-94.
Bailey, et al. "Convenient general method for the preparation of primary alkyllithiums by lithium-iodine exchange," (1990) J. Org. Chem. vol. 55, No. 19, pp. 5404-5406.
Barrans, et al., 1996, "Pre-beta HDL; structure and metabolism", Biochim, Biophys. Acta. 1300(2):73-85.
Becker, et al., 1982, "Intramolecular photoaddition of terminal allenes to conjugated cyclohexenones", J. Org. Chem. 47:3297-3310.
Beilstein Report for Compound Beilstein Registry No. 1741087, based in part on Crisan et al. (1956), Ann. Chim, (Paris), 13(1): 436-459.
Beilstein Report for Compound Beilstein Registry No. 1778991, based in part on Pechmann (1904), Chem. Ber., 37: 3819.

Beilstein Report for Compound Beilstein Registry No. 1784568, based in part on English (1941), J. Am. Chem. Soc., 63 (4): 941-943.
Beilstein Report for Compound Beilstein Registry No. 2961112, based in part on Lardelli et al. (1967), Recl. Tray. Chim., 86: 481-503.
Beilstein Report for Compound Beilstein Registry No. 5836264, based in part on Weber et al. (1992), J. Med. Chem., 35(21): 3755-3773.
Beilstein Report for Compound Beilstein Registry No. 7473723, based in part on Rieke et al. (1996), J. Org. Chem., 61(8): 2726-2730.
Beilstein Report for Compound, Beilstein Registry No. 5815199 based in part on Weber et al. (1992), J. Med. Chem., 35(21): 3755-3773.
Bernady, et al. "Prostaglandins and congeners. 20. Synthesis of prostaglandins via conjugate addition of lithium trans-1-alkenyltrialkylalanate reagents. A novel reagent for conjugate 1,4-additions," J. Org. Chem. (1979) vol. 44, No. 9, pp. 1438-1447.
Bhanot, et al. "Synthetic studies on Terpenoids. 5. Syntheses of γ- and δ-Lactones from β-(2,7-Dimethyl-1,2-dihdroxycycloheptyl)propionic Acid," J. Org. Chem. (1977) vol. 42, pp. 1623-1627.
Bicking, et al., "11,12-Secoprostaglandins. 1. Acylhydroxyalkanoic acids and related compounds", J. Med. Chem., 1977, pp. 35-43, vol. 20.
Bisgaier, et al., 1997, "Attenuation of plasma low density lipoprotein cholesterol by select 3-hydroxy-3-methylglutaryl coenzyme A reductase inhibitors in mice of low density lipoprotein receptors", J. Lipid Res. 38 (12):2502-2515.
Bisgaier, et al., 1998, "A novel compound that elevates high density lipoprotein and activates the peroxisome proliferator activated receptor", J. Lipid Res. 39(1):17-30.
Blatt ed., 1943, "Gilbert Sulfonation and Related Reactions" pp. 135-142, 160-165; Org. Synth. Coll. vol. II, Wiley, NY and Org. Synth. Coll. vol. IV, 1963, Wiley NY 529-531.
Blatt, et al., "The reducing action of Grignard reagent and the synthesis of tertiary aliphatic carbinols", J. Org. Chem., 1932, pp. 1495-1499, vol. 54.
Bohme, V. and Lener, W., 1955, Annalen der Chemie, 595;169-178 (Non-English Copy).
Bongini, et al., 1979 "A simple and practical method for tetrahydropyranylation of alcohols and phenols", Synthesis 618-620.
Brown, et al. "Selective reductions. 26. Lithuim triethylborohydride as an exceptionally powerful and selective reducing agent in organic synthesis. Exploration of the reactions with selected organic compounds containing representative functional groups," J. Org. Chem. (1980) vol. 45, No. 1, pp. 1-12.
Brown, H. C. et al. "Hydroboration. 67. Cyclic hydroboration of acyclic alpha,omega-dienes with 9-borabicyclo[3.3.1]nonane/borane-dimethyl sulfide," J. Org. Chem. (1984) vol. 49, No. 6, pp. 1072-1078.
Brown, H. C. et al. "Selective reductions. VII. Reaction of lithium trimethoxyaluminohydride with selected organic compounds containing representative functional groups," J. Am. Chem. Soc. (1965) vol. 87, No. 24, pp. 5614-5620.
Bruce, et al., 1998, "Plasma lipid transfer proteins, high-density lipoproteins, and reverse cholesterol transport", Annu Rev Nutr. 1998;18:297-330.
Campagna, et al., 1994, "Cyclic Amidine Analogues of Taurine and Homotaurine; Synthesis and Effects on Rat Skeletal Muscle", Farmaco, Ed. Sci 49:653-658.
Cerny, et al., 1969, "Properties of Sodium Bis-(2-Methoxyethoxy)-Aluminum Hydride", Collect Czech Chem Comm. 34:1025-33.
Chadwick, et al., 1979, "Reaction between N-Alkylpyroles and Alkyllithium Reagents" J. Chem Soc., Perkin Trans. 12845.
Chaikin, et al., 1949, "Lithium Borohydride as a Reducing Agent", J. Am. Chem. Soc. 71:3245-48.
Chen, et al., 1998, "Asymmetric total synthesis of phosphatidylinositol 3-phosphate and 4-phosphate derivatives", J. Org. Chem. 63:6511-22.

(56) References Cited

OTHER PUBLICATIONS

Comins, et al., 1981, "A one pot synthesis of unsymmetrical secondary alcohols from two grignard reagents", Tetrahedron Lett. 22:1085-88.
Corbridge, 1985, "Phosphorus: An Outline of its Chemistry, Biochemistry and Technology", Studies in Inorganic Chemistry, 3rd ed, pp. 357-395.
Corey, et al., 1967, "A useful method for the conversion of alcohols into iodides", J. Org. Chem. 32:4160-4161.
Corey, et al., 1979, "Useful procedures for the oxidation of alcohols involving pyridinum dichromate in aprotic media", Tetrahedron Lett. 5:399-402.
Carothers, 1924, "Platinum oxide as a catalyst in the reduction of organic compounds. V. The preparation of primary alcohols by the catalytic hydrogenation of aldehydes," J. Am. Chem. Soc. 46:1675-83.
Dalton, J.C. et al. (1971) "Type I and Type II Photochemical Reactions of Some Five- and Six-Membered Cycloalkanones," J. Am. Chem. Soc., 93 (26): 7213-21.
Danheiser, et al., 1991, "A Practical and Efficient Method for Synthesis of β-Lactones", J. Org. Chem. 58:1176-65.
Dansky HM, Fisher Ea, 1999, "High-density lipoprotein and plaque regression: the good cholesterol gets even better", Circulation 100(17): 1762-3.
Decossin, et al., 1997, "Subclasses of LpA-I in coronary artery disease: distribution and cholesterol efflux ability", Eur J Clin Invest. 27(4):299-307.
De Sarlo, et al., 1971, "Isoxazolin-5-one", J. Chem Soc. 88-89.
Eaton, et al., 1972, "Hydroxypropylation", J. Org. Chem. 37:1947-50.
Ehlinger, et al., 1980, "Silicon in Synthesis. 10. The (trimethylsiyl)allyl Anion: A. beta-Acyl anion equivalent for the conversion of aldehydes and ketones into gamma-lactone", J. Am. Chem. Soc. 102:5004-11.
Eisch, et al. 1978, "Synthesis of lactones via the titanium-catalyzed hydromagnesiation of alkenols", J. Organomet. Chem. 160:C8-C12.
Esperion Therapeutics Presents Full Results of Phase 2 Clinical Trial Showing Its Novel Oral Therapy ETC-1002 Lowered LDL-C by Up to 43 Percent in Hypercholesterolemic Patients with Type 2 Diabetes Data Presented at ATVB 2013 Scientific Sessions, May 2, 2013, 1-2.
Esperion Therapeutics Reports Second Quarter Financial Results and Provides Corporate Update, Aug. 12, 2013, 1-3.
Esperion Therapeutics Announces Positive Top-Line Results from Phase 2 Clinical Study of ETC-1002 as an Add-On to Statin Therapy in Patients with Hypercholesterolemia, Sep. 3, 2013, 1-2.
Fielding & Fielding, 1995, "Molecular physiology of reverse cholesterol transport", J. Lipid Res. 36(2):211-28.
Fraser, et al., 1985, "Acidity measurements in THF. V. Heteroaromatic compounds containing 5-membered rings", Can J. Chem. 63:3505-09.
Gearing, et al., 1993, "Interaction of the peroxisome-proliferator-activated receptor and retinoid X receptor", Proc. Natl. Acad. Sci. USA 90(4):14440-1444.
Gigg, et al., 1967, "The Preparation of Unsymmetrical Diglycerides", J. Chem. Soc., C. 431-434.
Gleiter, R. et al. "Synthesis and properties of 4,4,9,9-tetramethyl-1-oxa-cycloundecane-5,6,7,8-tetrone and 5,5,10,10-tetramethyl-1-oxa-cyclotridecane-6,7,8,9-tetrone," Chemistry—A European Journal (1996) vol. 2, No. 3, pp. 271-277.
Gleiter, R. et al., "Synthesis of 5,5,10,10-tetramethyl-1-oxacyclotridecane-6,7,8,9-tetrone—on the mechanism of the Rubotom reaction," Eur. J. Org. Chem. (1995) No. 9, pp. 1655-1661.
Green and Kehinde, 1975, "An established predispose cell line and its differentiation in culture II. Factors affecting the adipose conversion", Cell. 5(1):19-27.
Greene, T.W., 1999, "Protection for the Hydroxyl Group, Including 1,2-and 1,3-Diols", Protective Groups in Organic Synthesis.

Harris and Kletzien, 1994, "Localization of pioglitazone response element in the adipocyte fatty acid-binding protein gene", Mol Pharmacol. 45(3):439-45.
Hayden and Ma, 1992, "Molecular genetics of human lipoprotein lipase deficiency", Mol Cell Biochem. 113(2):171-6.
Heyman, et al., 1992, "9-cis retinoic acid is high affinity ligand for the retinoid X receptor", Cell 68(2):397-406.
Hidaka and Fidge, 1992, "Affinity purification of the hepatic high-density lipoprotein receptor identifies two acidic glycoproteins and enables further characterization of their binding properties", Biochem. J. 15(Pt1):161-7.
Hirano, et al., 1997, "Genetic cholesteryl ester transfer deficiency is extremely frequent in the Omagari area of Japan. Marked hyperalphalipoproteinema caused by CETP gene mutation is not associated with longevity", Arterioscler. Thromb. Vasc.Biol. 17(6):1053-1059.
Hoyer, et al., 1986, "Catalysis by acidic clay of the protective tetrahydropyranylation of alcohols and phenols", Synthesis 655-57.
Hudlicky, M., 1996, "Reduction of aldehydes and their derivatives", Reductions in Organic Chemistry, 2nd ed. pp. 137-139.
Hudlicky, M., 1996, "Reduction of esters and lactones of carboxylic acids", Reduction in Organic Chemistry 2nd ed. pp. 212-217.
International Preliminary Report, International Application No. PCT/US2018/034646, dated Dec. 5, 2019 (7 pages).
International Search Report and the Written Opinion of the International Search Authority, or the Declaration, Int'l Application No. PCT/US18/17434, dated Apr. 19, 2018, 16 pages.
International Search Report, International Application No. PCT/US2003/041411, dated Dec. 8, 2004 (12 pages).
Ishibashi, et al., 1993, "Hypercholesterolemia in low density lipoprotein receptor knockout mice and its reversal by adenovirus-mediated gene delivery", J. Clin. Invest. 92(2):883-93.
Ishibashi, et al., 1994, "Massive xanthomatosis and atherosclerosis in cholesterol-fed low density lipoprotein receptor-negative mice", J. Clin Invest. 93(5):1885-93.
Isseman and Green, 1990, "Activation of a member of the steroid hormone receptor superfamily by peroxisome proliferators", Nature 347(6294):645-650.
Iwai, et al, 1966, "Studies on acetylenic compounds. XLIV. Synthesis of 3-aminoisoxazoles and 3-hydroxyisoxazoles (3-Isoxazolones)", Chem. Pharm. Bull. 14:1277-88.
Jetter, R., "Long-chain alkanediols from Myricaria germanica leaf cuticular waxes," Phytochemistry, 55 (2), 2000, pp. 169-176.
Johnston, et al., 1988, "A new, mild heterogeneous catalyst for the tetrahydropyranylation of alcohols and phenols", Synthesis 393-4.
Katritzky, et al., 1993, "Generation and Reactions of sp2-Carbanionic Centers in the Vicinity of Heterocyclic Nitrogen Atoms", Adv. Het. Chem. 56:155-303.
Katsiki et al., "Non-alcoholic Fatty Liver Disease and Dyslipidemia: An Update," 2016, Metabolism, 65(8), pp. 1109-1123.
Keller and Wahli, 1993, "Peroxisome proliferator-activated receptors-A link between endocrinology and Nurition?" TEM, 4:291-295.
Keller, et al., 1993, "Fatty acids and retinoids control lipid metabolism through activation of peroxisome proliferator-activated receptor-retinoid X receptor heterodimers", Proc. Natl. Acad. Sci. USA 90(6):2160-2164.
Kessar, et al., 1997, "Lewis acid complexation of tertiary amines and related compounds: A strategy for a α-deprotonation and stereocontrol", Chem. Rev. 97:721-37.
Kletzein, et al., 1991, "Enhancement of adipocyte differentiation by an insulin-sensitizing agent", Mol Pharmacol 41(2):393-398.
Kliewer, et al., 1992, "Convergence of 9-cis retinoic acid and peroxisome proliferator signaling pathways through heterodimer formation of their receptors", Nature 27;358(6389):771-4.
Kurata, et al., 1998, "A candidate high density lipoprotein (HDL) receptor, HB2, with possible multiple functions shows sequence homology with adhesion molecules", J. Atherosclerosis and Thrombosis 4(3):112-7.
Kurz, et al., 1985, "Anomalous selectivities in methyl transfers to water: An explanation using free energy surfaces which model the effects of non-equilibrium solvation", Isr. J. Chem. 26:339-48.

(56) References Cited

OTHER PUBLICATIONS

Kurz, et al.. "Evidence for rate-determining solvation change in methyl transfer to water. Solvent dependence of H2O/D2O kinetic isotope effects," J. Am. Chem. Soc. (1986) vol. 108, pp. 2960-2968.
Lagrost, et al., 1996, "Opposite effects of cholesteryl ester transfer protein and phospholipid transfer protein on the size distribution of plasma high density lipoproteins. Physiological relevance in alcoholic patients", J. Biol. Chem.271(32):19058-65.
Landshultz, et al., 1996, "Regulation of scavenger receptor, class B, type I, a high density lipoprotein receptor, in liver and steroidogenic tissues of the rat", J. Clin. Invest. 98(4):984-995.
Larock, 1989, Comprehensive Organic Transformations; Ch. 6, VCH: New York, pp. 446-448.
Lazarow and Fujiki, 1985, "Biogenesis of peroxisomes", Annu Rev Cell Biol. 1:489-530.
Levin, et al., 1992, "9-cis retinoic acid stereoisomer binds and activates the nuclear receptor RXR alpha", Nature 355(6358):359-61.
Ludwig, et al., 1989, "Rapid and efficient synthesis of nucleoside 5'-0-(1-thiotriphosphates), 5'-triphosphates and 2',3'-Cyclophosphorothioates using 2-Chloro-4H-1,3,2-benzodioxaphosphorin-4-one", J. Org. Chem. 54:631-35.
Maddaford, et al., 1993, "A general asymmetric synthesis of (-)-alpha-Dimethylretrodendrin and its diastereomers", J. Org. Chem 58:4132-38.
March, J., 1992, Advanced Organic Chemistry: Reactions, Mechanisms, and Structure 4th ed., pp. 248-272, 1196-1198, 437-438, 920-929.
Masamune, et al. "Tylonolide hemiacetal, the aglycone of tylosin, and its partial synthesis," J. Am. Chem. Soc. (1976) vol. 98, No. 24, pp. 7874-7875.
Masayuma, et al., 2000, "Regio-and diastereocontrol in carbonyl allylation by 1-halobut-2-enes with Tin(II) halides", J Org Chem. 65(2):494-8.
McCune et al., "Effect of Mevinolin on Cholesterol Metabolism in Obese and Lean Zucker Rats," Biochemical Pharmacology (1987) vol. 36, pp. 875-879. (abstract only).
Menger, et al., 1981, "Synthetically useful oxidations at solid sodium permanganate surfaces", Tetrahedron Lett. 22:1655-56.
Miyashita, et al., 1977, "Pyridinium .rho.-Toluenesulfonate. A mild and efficient catalyst for the tetrahydropyranylation of alcohols", J. Org. Chem 42:3772-74.
Moffet, et al., 1963, "2-(1-Pyrrolidyl)Propanol", Org. Synth. Collect 4:834-5.
Mulzer, 1995, Comprehensive Organic Functional Group Transformations Oxford 5 pp. 161.
Myers, et al., 1992, "Studies on the thermal generation and reactivity of a class of (.alpha., .pi.)-1,4-biradicals", J. Am. Chem. Soc. 114:9369-86.
Nagano H., et al., "Stereoselectivitiy in the formation and radical reduction of cyclic bromoacetals, key intermediates for the synthesis of delta-hydroxy-and epilson-hydroxy-alpha-methylcarboxylic acid esters", Tetrahedron Letters, 2003, pp. 6867-6870, vol. 44, No. 36.
Nan F. et al. "Dual Function Glutamate-Related Ligands: Discovery of a Novel, Potent Inhibitor of Glutamate Carboxypeptidase II Possessing mGluR3 Agonist Activity" Journal of Medicinal Chemistry 2000, 43:pp. 772-774.
Nemali, et al., 1988, "Comparison of constitutive and Inducible levels of expression of paroxisomal beta-oxidation and catalase genes in liver and extrahepatic tissues of rat", Cancer Res. 48(18):5316-24.
Nystrom, et al., 1947, "Reduction of Organic Compounds by Lithium Aluminum Hyride", J. Am. Chem. Soc. 69:1197-1199.
Nystrom, et al., 1949, "Lithium borohydride as a reducing agent", J. Am. Chem. 71:3245-47.
Office Action, U.S. Appl. No. 15/125,401, dated Nov. 6, 2018, 14 pages.
Office Action, U.S. Appl. No. 15/125,401, dated Feb. 16, 2018, 10 pages.
Office Action, U.S. Appl. No. 15/558,519, dated Apr. 4, 2018, 5 pages.
Office Action, U.S. Appl. No. 15/859,279, dated Jun. 27, 2019, 35 pages.
Office Action, U.S. Appl. No. 15/859,279, dated May 24, 2018, 28 pages.
Office Action, U.S. Appl. No. 15/859,279, dated Nov. 29, 2018, 34 pages.
Ogata, et al., 1969, "Kinetics of the Baeyer-Villiger reaction of benzaldehydes with perbenzoic acid in aquoorganic solvents", J. Org. Chem. 34:3985-91.
Okamoto, et al., 1985, "Synthesis of Alkyl Dihydrogenphosphate by the Reaction of Alcohols and Silyl Polyphosphate", Bull Chem. Soc. Jpn. 58:3393-3394.
Olah, et al., 1979, "Transformations with Chlorotrimethylsilane/ Sodium Iodide, a Convenient In Situ Iodotrimethylsilane Reagent", J. Org. Chem 44:8, 1247-1251.
Olah, et al., 1984, "N-Formylmorpholine: A New and Effective Formylating Agent for the Preparation of Aldehydes and Dialkyl(1-Formylalkyl)phosphonates from Grignard or Organolithium Reagents", J. Org. Chem. 4.
Olah, et al., 1987, "Formylating Agents", Chem. Rev. 87:4, 671-686.
Oster, et al., 1983, "Generation and Reactions of the Dianion of 3-Hydroxy-5-methylisoxazole, a convenient β-keto Amide Synthon", J. Org. Chem 48:4307-4311.
Parra, et al., 1992, "A case-control study of lipoprotein particles in two populations at contrasting risk for coronary heart disease. The ECTIM Study", Arterioscler Thromb. 12:701-707.
PCT International Search Report and Written Opinion, PCT Application No. PCT/US2015/021677, dated Apr. 16, 2015, 8 pages.
Pop, et al., 1997, "Allylic and Phenolic Phosphate Esters of Dexanabinol", Org. Prep. And Proc. Int. 29:341-347.
Ramirez, et al. "Phosphorylation by means of cyclic enediol phosphates," Acc. Chem. Res. (1978) vol. 11, pp. 239.
Raunio, et al., 1957, "Addition of Propargyl Acetal to Cyclohexanone in the Presence of Sodamide", J. Org. Chem 22:570.
Reaven, 1993, "Role of Insulin resistance in human disease (syndrome X): an expanded definition", Annu Rev Med. 44:121-31.
Reddy and Lalwani, 1983, "Carcinogenesis by hepatic peroxisome proliferators: evaluation of the risk of hypolipidemic drugs and industrial plasticizers to humans", Crit Rev Toxicol. 12(1):1-58.
Remington, The Science and Practice of Pharmacy, Nineteenth Edition-1995, p. 710-712; pp. 1615-1617.
Rigotti, et al., 1996, "Regulation by adrenocorticotropic hormone of the in vivo expression of scavenger receptor class B type I (Sr—Bi), a high density lipoprotein receptor, in steroidogenic cells of the murine adrenal", J. Biol. Chem. 1996, vol. 271(52):33545-9.
Robins and Fasulo, 1997, "High density lipoproteins, but not other lipoproteins, provide a vehicle for sterol transport to bile", J Clin Invest. 98(3):380-4.
Rowe, "Handbook of Pharmaceutical Excipients, 6th Ed." 2009, Pharmaceutical press, pp. 129-133, 185-188, 317-324, 364-369, 404-407, 581-585, 651-653 and 663-666.
Sam, et al., 1972, "Crown Polyether Chemistry, Potassium Permanganate Oxidations in Benzene", J. Am. Chem. Soc. 94:4024.
Saulnier, et al., 1982, "Generation and Reactions of 3-Lithio-1-(phenylsulfonyl)Indole", J. Org. Chem 47:757.
Schaper, U.A. (1980) "Die gemischte Guerbet-Reaktion zwischen cyclischen and acyclischen Alkoholen," Fette, Seifen, Anstrichmittel, Industrieverlag von Hernhaussen kg, 82 (11): 454-456.
Shen, "Cover Up," Innovations in Pharm Tech 52, (2015), pp. 44-47.
Shirley, et al., 1995, "Metalation of pyrrole, 1-methylpyrrole, and 1-phenylpyrrole with n-Butyllithium", J. Org. Chem 20:225-31.
Silverman, The Organic Chemistry of Drug Design and Drug Interaction, 1992, pp. 15-22.
Skinner, et al., 1995, "Benzoylcyanamide from ethyl benzoylitioncarbomate", J. Am. Chem. Soc. 77:5440-42.
Smith, et al., 1957, "Nitrogen Compounds of the phosphoric and Phosphonic Acids, III, Preparation and Properties of Amides of Phenylphosphonic and Phenylphosphonothiolic Acids", J. Org. Chem. 22:265-267.

(56) References Cited

OTHER PUBLICATIONS

Song, et al., 1999, "Practical asymmetric synthesis of an endothelin receptor antagonist", J. Org. Chem. 64:9658-67.
Staels and Auwerx, 1998, "Regulation of apo A-I gene expression by fibrates", Atherosclerosis 137 Suppl:S19-23.
Stevens, et al., 1982, "Further studies on the utility of sodium hypochlorite in organic synthesis Selective oxidation of diols and direct conversion of aldehydes to esters," Tetrahedron Lett. 23:4647-4650.
Stowell, et al., 1995, "A new method for the phosphorylation of alcohols and phenols", Tetrahedron Lett. 36(11):1825-26.
Sundararaman, et al., 1978, "One step conversion of aldehydes to esters", Tetrahedron Lett. 19:1627-1628.
Sweeney, 1995, "Comprehensive Organic Functional Group Transformations", Oxford, vol. 2, pp. 104-109.
Taravel, et al., 1988, "Interglycosidic 13C-1H Coupling Constants", Tetrahedron Lett. 29:199-200.
Thompson et al., "Treatment with ETC-1002 along in in combination with ezetimibe lowers LDL cholesterol in hypercholesterolemic patients with or without statin intolerance," 2016, National Lipid Association, Journal of Clinical Lipidology, vol. 10, pp. 556-567.
Thums et al., "Epoxidation—a Consequence of Cell Damage," Chemical Monthly, 128 (4), 1997, pp. 411-420.
Kanai and Tomioka, "Catalytic Asymmetric Conjugate Addition of Grignard Reagents Mediated by Copper (I)-Chiral Bidentate Phosphine Complex", Tetrahedron Lett. 36:4275-4278; 1995.
Tontonoz, et al., 1994, "Adipocyte-specific transcription factor ARF6 is a heterodimeric complex of two nuclear hormone receptors, PPAR gamma and RXR alpha", Nucleic Acids Res. 22(5):5628-5634.
Uhlmann, et al., 1986, "Chemical 5'-phosphorylation of oligonucleotides valuable in automated DNA synthesis", Tetrahedron Lett. 27:1023-26.
Ulrich, et al., 1995, "Cultured hepatocytes as investigational models for hepatic toxicity: practical applications in drug discovery and development", Toxicol Lett. 82/83:107-15.
Urata, et al., 1991, "Transition metal complex catalyzed carbonylation of organic halides in the presence of molecular sieves instead of base," Tetrahedron Lett. 32:36, 4733-36.
Vamecq and Draye, 1989, "Pathophysiology of peroxisomal .beta.-oxidation", Essays Biochem. 24: 115-225.
Vippagunta, S. et al., "Crystalline Solids," Advanced Drug Delivery Reviews (2001) vol. 48, pp. 2-26. (abstract only).
Vogtle, et al., 1987, "Doubly Clamped Cope Systems", J. Org. Chem. 52:5560-5564.
Williams, et al., 1988, "Bromine as an oxidant for direct conversion of aldehydes to esters", Tetrahedron Lett. 29:5087-90.
Wilson, et al., 1982, "A novel, nonoxidative method for the conversion of aldehydes to esters", J. Org. Chem. 47:1360-61.
Wroblewski and Ladue, 1995, "Lactic dehydrogenase activity in blood", Proc. Soc. Exp. Biol. Med. 90:210-213.
Xu, et al., 1989, "The retinoblastoma susceptibility gene product: a characteristic pattern in normal cells and abnormal expression in malignant cells", Onocogene 4: 807-812.
Yamamoto, "Asymmetric synthesis of 5-and 6-membered lactones from cyclic substrates bearing a C2-chiral auxiliary", J. Org. Chem., 1991, pp. 1112-1119, vol. 35, No. 21.
Yanagisawa, et al., 1994, "Allylbarium Reagents: Unprecedented regio- and stereoselective allylation reactions of carbonyl compounds", J. Am. Chem. Soc. 116:6130-6141.
Yoshikawa, et al., 1983, "Catalytic Regioselective Dehydrogenation of Unsymmetrical alpha Omega-Diols Using Ruthenium Complexes", Tetrahedron Lett. 26:2677-2680.
Yu, et al., 1988, "A novel reagent for the synthesis of myo-inositol phosphates: N,N-diisopropyl dibenzyl phosphoramidite", Tetrahedron Lett. 29:979-82.
Yunker, et al., 1978, "Alpha-oxygenated fatty acids occurring as amides of 2-methylene beta-alanine in a marine sponge", Tetrahedron Lett. 47:4651-52.
Cilla et al., "Multiple-dose Pharmacokinetics, Pharmacodynamics, and Safety of Atorvastatin, an Inhibitor of HMG-CoA Reductase, in Healthy Subjects," Clinical Pharmacology & Therapeutics 60(6): 687-695 (1996).
Gray et al.,"Comparison of Sequential Rosuvastatin Doses in Hypercholesterolaemia: a Meta-analysis of Ramdomised Controlled Trials," Current Medical Research and Opinion 26(3):537-547 (2010).
Hu et al.,"Safety of Statins: an Update," Ther. Adv. Drug Saf. 3(3):133-144 (2012).
Jacobson, The Safety of Aggressive Statin Therapy: How Much Can Low-Density Lipoprotein Cholesterol Be Lowered? Mayo Clin. Proc. 81(9):1225-1231 (2006).
Martin et al., "A Double-Blind, Randomized, Incomplete Crossover Trial to Assess the Dose Proportionality of Rosuvastatin in Healthy Volunteers," Clinical Therapeutics 25 (8):2215-2224 (2003).
Thompson et al., "Use of ETC-1002 to Treat Hypercholesterolemia in Patients with Statin Intolerance," Journal of Clinical Lipidology 9:295-304 (2015).

\* cited by examiner

FIXED DOSE COMBINATIONS AND FORMULATIONS COMPRISING ETC1002 AND ONE OR MORE STATINS AND METHODS OF TREATING OR REDUCING CARDIOVASCULAR DISEASE

CROSS REFERENCE TO RELATED APPLICATIONS

This application is a U.S. national stage application under 35 U.S.C. § 371 of International Application No. PCT/US2016/022694, filed Mar. 16, 2016, which claims the benefit of U.S. Provisional Application No. 62/133,739, filed Mar. 16, 2015, and U.S. Provisional Application No. 62/277,403, filed Jan. 11, 2016, each of which is hereby incorporated in its entirety by reference.

BACKGROUND

Field of the Invention

This application relates to methods and compositions useful for treating cardiovascular conditions or reducing the risk of cardiovascular conditions. Statins are a cornerstone of prevention and treatment of cardiovascular disease, however, cardiovascular disease remains amongst the top leading causes of death in the United States and other countries around the world. Millions of people, in the United States alone, suffer from a cardiovascular disease or disorder.

Low-density lipoprotein cholesterol (LDL-C) is a well-established risk factor for cardiovascular disease. However, many patients, for example those with hypercholesterolemia, fail to reduce LDL-C to desired levels with traditional therapies. Existing residual cardiovascular risk, especially observed in high-cholesterol patients, and despite the advances of new cholesterol-reducing drugs, has encouraged a search for new, non-traditional pharmaceuticals. New pharmaceutical drugs have been developed and are effective at reducing cholesterol levels in the human body. Unfortunately, these drugs also induce negative side-effects. Many of the compounds which have shown to be potent for inhibiting the enzymes of cholesterol biosynthesis are also systemically toxic. Thus, there is a need for new pharmaceutical formulations which are both effective and safe for reducing cholesterol.

SUMMARY

This application relates to methods and compositions comprising fixed doses of ETC-1002 and statins for the treating or reducing the risk of cardiovascular disease.

ETC-1002 (bempedoic acid) is an oral, once-daily therapy which lowers cholesterol by inhibiting adenosine triphosphate (ATP) citrate lyase (ATPCL). ATPCL is farther upstream than HMG-CoA reductase in the cholesterol biosynthetic pathway.

ETC-1002 lowers low-density lipoprotein cholesterol (LDL-C) by direct inhibition of hepatic adenosine triphosphate citrate lyase, leading to reduced de novo cholesterol synthesis and increased LDL receptor expression. ETC-1002 administered in doses from 120 mg to 240 mg daily reduced LDL-C by 27% to 43% in phase 2a clinical trials of various hypercholesterolemic populations including patients with type 2 diabetes mellitus and patients with muscle-related statin intolerance.

The general class of "statins" are compounds which lower cholesterol levels in the body by inhibiting the enzyme 3-hydroxy-3-methylglutaryl-coenzyme A (HMG-CoA) reductase and concomitantly, the pathway for synthesizing cholesterol in the liver. Examples of compounds which are part of the "stain" class include, but are not limited to, atorvastatin, simvastatin, rosuvastatin, and pravastatin. Treatments usually administer from about 2 mg to 80 mg of a statin compound.

The inventors have found that HMG-CoA reductase inhibition leads to an increase in LDL receptor activity. Additionally, the inventors find that combining these two therapies leads to cooperative activity and favorable clinical treatment. Accordingly, the present invention is directed toward cholesterol-lowering compositions comprising statins and ETC-1002. These compositions lead to further reductions in total cholesterol, and specifically LDL-C, in patients.

The present application also discloses a method of lowering cholesterol using fixed dose combination of ETC-1002 and one or more statins. Based on observations in on-going studies, combination therapy with ETC-1002 and a fixed, high dosage of one or more statins has comparable efficacy and safety to that of ETC-1002 combined with a fixed, low to medium dosage of one or more statins. Of course combination therapy with ETC-1002 and a fixed, high dosage of one or more statins is also significantly greater versus statin or ETC-1002 monotherapy (120 mg or 180 mg daily) in patients with or without a history of statin-related muscle symptoms. The combination therapy shows a significantly greater efficacy and safety profile even in acute hypercholesterolemic patients.

In one aspect, methods and compositions of present invention even lower cholesterol in patients with persistently elevated LDL-C, despite stable statin therapy at this high of a dosage.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Advantages and Utility

Figure 1:
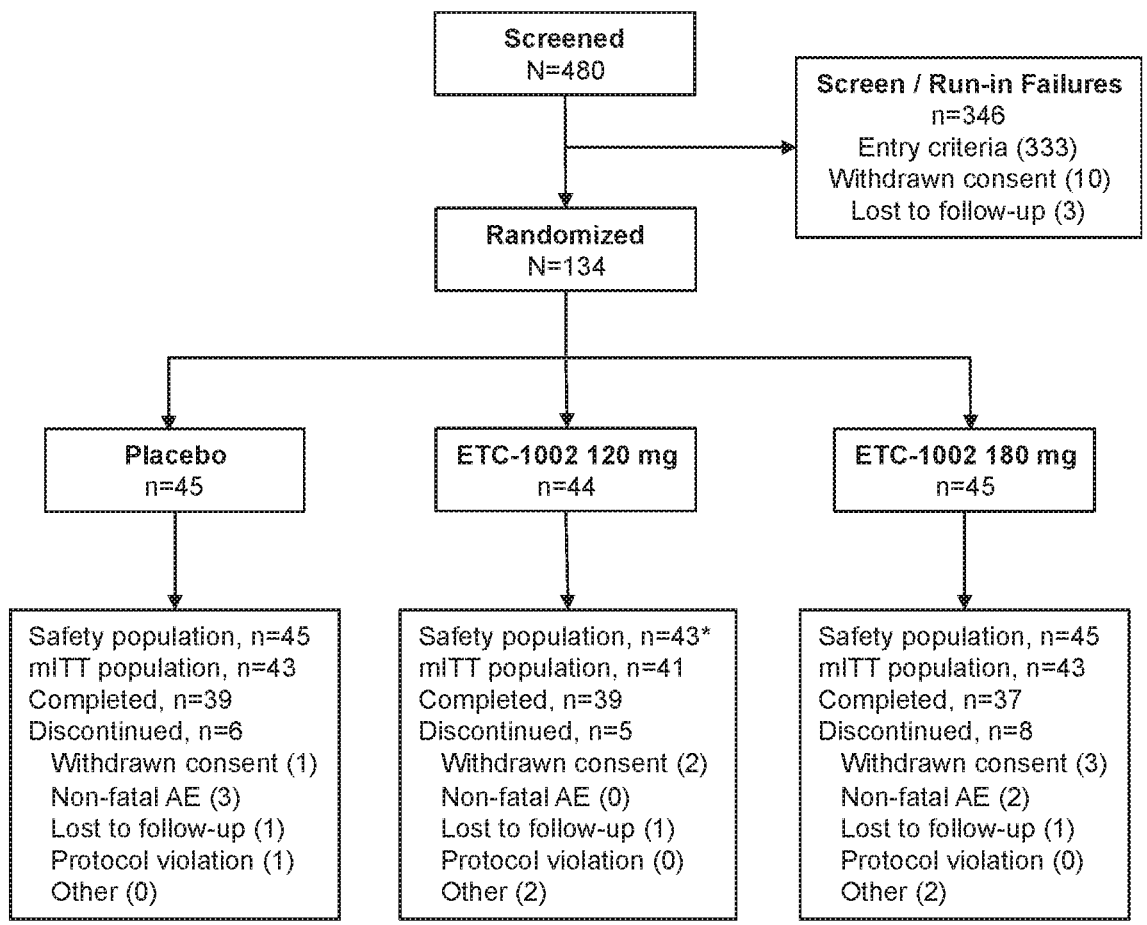
FIG. 1: Disposition of Patients. *One patient was randomized but discontinued before receiving study drug. AE=adverse event; mITT=modified intent to-treat.
Figure 2:
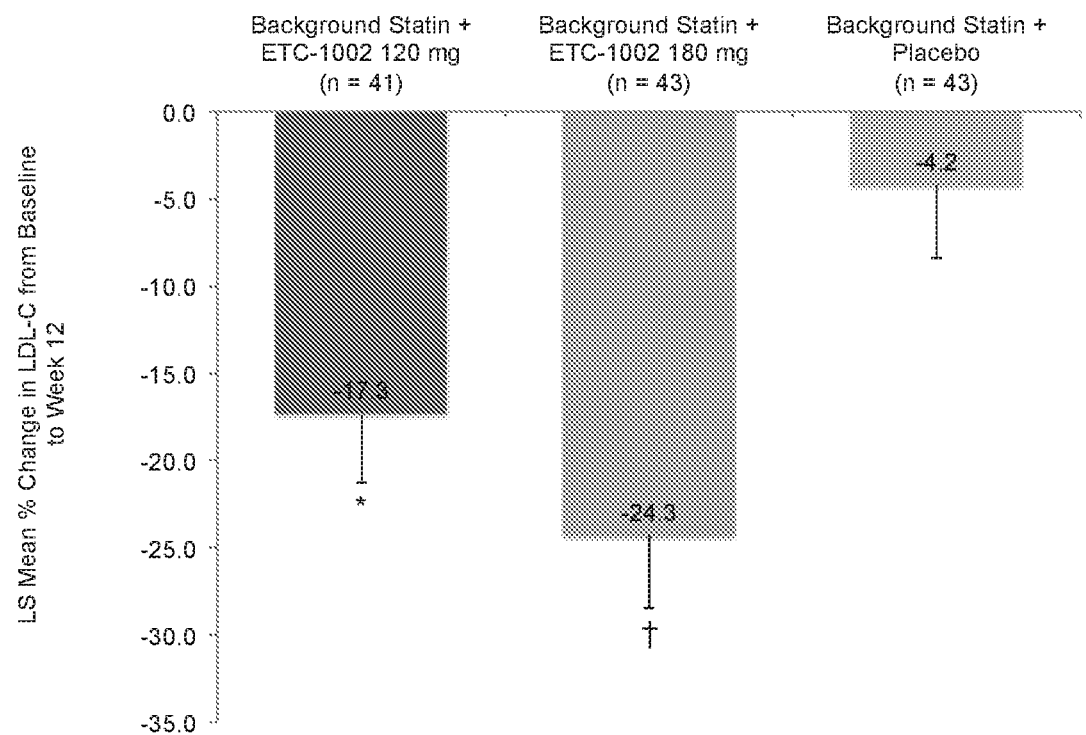
FIG. 2: Mean Percent Change in LDL-C from Baseline to Week 12. These data are from the modified intent-to-treat population. LDL-C=low-density lipoprotein cholesterol; LS=least-squares. *p=0.0055 vs placebo; †p<0.0001 vs placebo. Error bars represent standard error.

Briefly, and as described in more detail below, described herein are compositions, methods of making the said compositions and methods for treating cardiovascular disease or reducing the risk of cardiovascular disease using fixed-dose combinations of one or more statins and ETC-1002. The advantages for this approach are numerous and include, but are not limited to, increased reduction of cholesterol and low density lipoprotein levels in patients treated with the fixed-dose combinations of one or more statins and ETC-1002 than when patients are treated with either statins or ETC-1002 alone. As described above, statins are the cornerstone of prevention and treatment of cardiovascular disease, but can produce unwanted side effects in many patients. Such side effects include, but are not limited to, increased concentrations of liver enzymes, muscle problems, and an increased risk of diabetes. Statin-associated muscle symptoms are an important clinical problem because statin discontinuation in hypercholesterolemic patients increases cardiovascular risk. Hence, there is a significant need for cardiovascular therapies for patients that exhibit muscle-related statin intolerance.

Definitions

Terms used in the claims and specification are defined as set forth below unless otherwise specified.

Terms used in the claims and specification are defined as set forth below unless otherwise specified. Further, if any term or symbol used herein is not defined as set forth below, it shall have its ordinary meaning in the art.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Generally, reference to a certain element such as hydrogen or H is meant to include all isotopes of that element. For example, if an R group is defined to include hydrogen or H, it also includes deuterium and tritium. Compounds comprising radioisotopes such as tritium. $C^{14}$, $P^{32}$ and $S^{35}$ are thus within the scope of the present technology. Procedures for inserting such labels into the compounds of the present technology will be readily apparent to those skilled in the art based on the disclosure herein.

The term "ameliorating" refers to any therapeutically beneficial result in the treatment of a disease state, e.g., an inflammatory disease state, including lessening in the severity or progression, remission, or cure thereof. In some embodiments, "ameliorating" includes prophylaxis of a disease state.

The term "in vitro" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can, in some embodiments, be a "prophylactically effective amount" as prophylaxis can be considered therapy.

The compounds of the present technology can exist as solvates, especially hydrates. Hydrates may form during manufacture of the compounds or compositions comprising the compounds, or hydrates may form over time due to the hygroscopic nature of the compounds. Compounds of the present technology can exist as organic solvates as well, including DMF, ether, and alcohol solvates among others. The identification and preparation of any particular solvate is within the skill of the ordinary artisan of synthetic organic or medicinal chemistry.

"Subject" refers to a mammalian organism treated using a compound of the present invention. The "subject" can be a human or non-human mammalian organism.

"Tautomer" refer to alternate forms of a compound that differ in the position of a proton, such as enol-keto and imine-enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

"Treating" or "treatment" of a disease or disorder in a subject refers to 1) preventing the disease or disorder from occurring in a subject that is predisposed or does not yet display symptoms of the disease or disorder; 2) inhibiting the disease or disorder or arresting its development; or 3) ameliorating or alleviating the cause of the regression of the disease or disorder.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

Unless defined otherwise, all technical and scientific terms used herein have the meaning commonly understood by a person skilled in the art to which this invention belongs.

Herein any and all heteroaryl and heterocycloalkyl substituents may contain up to four heteroatoms selected from the group consisting of: O, N, and S.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be substituted one more time (at from one to three positions).

It is understood that the above definitions are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Abbreviations

AE is an abbreviation for adverse event
CK is an abbreviation for creatine kinase
HDL-C is an abbreviation for high-density lipoprotein cholesterol
CRP=is an abbreviation for high-sensitivity C-reactive protein
LDL-C is an abbreviation for low-density lipoprotein cholesterol
LS is an abbreviation for least-squares
NCEP ATP-III is an abbreviation for National Cholesterol Education Program Adult Treatment Panel III
non-HDL-C is an abbreviation for non-high-density lipoprotein cholesterol
VLDL is an abbreviation for very-low-density lipoprotein
Therapy Disclosed herein is a method comprising administrating a fixed-dose combination of a fixed dose of ETC-1002 or an analog thereof and a fixed dose of one or more statins or an analog thereof to a subject in need thereof, optionally wherein ETC-1002 is administered at a fixed dose of 180 mg or at a fixed dose of 120 mg and each one of the one or more statins is administered at a fixed dose from 2 to 80 mg, optionally wherein the method decreases the level of low density lipoprotein cholesterol (LDL-C) in the subject below that of a control subject receiving a placebo, a fixed 120 mg dose of ETC-1002, a fixed 180 mg dose of ETC-1002, or a fixed dose between 2 to 80 mg of each one of the one or more statins, and optionally wherein the method treats or reduces the risk of cardiovascular disease in the subject.

In some aspects, ETC-1002 is administered at a fixed dose of 180 mg or at a fixed dose of 120 mg and each one of the one or more statins is administered at a fixed dose from 2 to 80 mg.

In some aspects, the subject has hypercholesterolemia, and wherein the method further comprises treating hypercholesterolemia.

In some aspects, the method treats or reduces the risk of cardiovascular disease in the subject.

In some aspects, the method decreases the level of cholesterol in the subject below that of a control subject receiving a placebo, a fixed 120 mg dose of ETC-1002, a fixed 180 mg dose of ETC-1002, or a fixed dose from 2 to 80 mg dose of each one of the one or more statins.

In some aspects, the method decreases the level of LDL-C in the subject below that of a control subject receiving a placebo, a fixed 120 mg dose of ETC-1002, a fixed 180 mg dose of ETC-1002, or a fixed dose from 2 to 80 mg dose of each one of the one or more statins. In some aspects, the method decreases the level of C-reactive protein (hsCRP) in the subject below that of a control subject receiving a placebo, a fixed 120 mg dose of ETC-1002, a fixed 180 mg dose of ETC-1002, or a fixed dose from 2 to 80 mg dose of each one of the one or more statins. In some aspects the reduction of C-reactive protein is up to 20% or 30% or more relative to baseline. In some aspects, the method decreases the level of apolipoprotein B (ApoB) in the subject below that of a control subject receiving a placebo, a fixed 120 mg dose of ETC-1002, a fixed 180 mg dose of ETC-1002, or a fixed dose from 2 to 80 mg dose of each one of the one or more statins. In some aspects, the method decreases the level of non-high density lipoprotein-cholesterol in the subject below that of a control subject receiving a placebo, a fixed 120 mg dose of ETC-1002, a fixed 180 mg dose of ETC-1002, or fixed dose from 2 to 80 mg for each one of the one or more statins. In some aspects, the method decreases the LDL particle number in the subject below that of a control subject receiving a placebo, a fixed 120 mg dose of ETC-1002, a fixed 180 mg dose of ETC-1002, or a fixed dose from 2 to 80 mg for each one of the one or more statins.

In some aspects, the method dose dependently reduces apolipoprotein B by 15% to 17% or more, non-high-density lipoprotein cholesterol by 14% to 17% or more, total cholesterol by 13% to 15% or more, and LDL particle number by 17% to 21% or more.

In some aspects, LDL-C is decreased in the subject up to 24% or more relative to baseline. In some aspects, non HDL-C is decreased in the subject by at least 30, 35, 37, 40, 42, or 45% or more relative to baseline. In some aspects, hsCRP is decreased in the subject by at least 20, 25, 26, 30, 35, 38, or 40% or more relative to baseline.

In some aspects, non-HDL-C is decreased in the subject by at least 30, 35, 40, 43, 45, 48, or 50% or more relative to baseline. In other aspects, HDL-C is decreased in the subject relative to baseline.

In some aspects, Statin and ETC-1002 are each administered orally. In some aspects, one or more statins and ETC-1002 are each administered at least once daily. In some aspects, one or more statins and ETC-1002 are each administered at least once daily for at least 1, 2, 3, 4, 5, 6, 7, 8, 9, 10, 11, or 12 week(s).

In some aspects, the subject has dyslipidemia. In some aspects, the subject has hypercholesterolemia. In some aspects, the subject is obese, optionally wherein the BMI of the subject is 18-45 kg/m$^2$. In some aspects, the subject is statin tolerant. In some aspects, the subject is statin intolerant. In some aspects, the subject experiences an adverse event when on one or more statins at the lowest FDA approved dose, said adverse events being selected form the group consisting of muscle-related pain, aches, weakness, and cramping. The inventors have observed that such muscle-related adverse events that began or increased during statin therapy could be significantly lowered or even resolved when treatment with add on ETC-1002 therapy to statin therapy was employed.

In some aspects, the subject has a baseline LDL-C level of 115-220 mg/dL. In some aspects, the subject has a baseline triglycerides level of less than or equal to 400 mg/dL.

In some aspects, one or more statins and ETC-1002 are administered simultaneously. In some aspects, one or more statins and ETC-1002 are administered separately.

Also disclosed herein is a method of treating cardiovascular disease or reducing the risk of cardiovascular disease in a subject, comprising administrating a fixed-dose combination of a fixed dose of ETC-1002 or an analog thereof and a fixed dose of one or more statins or an analog thereof to a subject in need thereof, optionally wherein ETC-1002 is administered at a fixed dose of 120 mg or at a fixed dose of 180 mg and each one of the one or more statins is administered at a fixed dose of between 2-80 mg, optionally wherein the method decreases the level of low density lipoprotein cholesterol (LDL-C) in the subject below that of a control subject receiving a placebo, a fixed 120 mg dose of ETC-1002, a fixed 180 mg dose of ETC-1002, or a fixed 2-80 mg dose of each one of one or more statins, and optionally wherein the subject has hypercholesterolemia.

Also disclosed herein is a pharmaceutical composition comprising ETC-1002 and one or more statins, optionally wherein ETC-1002 is present at a fixed dose of 120 mg or 180 mg and each one of the one or more statins is present at a fixed dose between 2-80 mg.

In some aspects, the composition further comprises a pharmaceutically acceptable vehicle. In some aspects, ETC-1002 is present at a fixed dose of 120 mg or 180 mg and each one of the one or more statins is present at a fixed dose between 2-80 mg. In some aspects, the composition is formulated for oral delivery. In some aspects, the composition is formulated for administration once daily.

In some aspects, the method decreases the level of apolipoprotein B (ApoB) in the subject below that of a control subject receiving a placebo, a fixed 120 mg dose of ETC-1002, a fixed 180 mg dose of ETC-1002, or a fixed 2-80 mg dose for each one of one or more statins.

In some aspects, the method decreases the level of apolipoprotein A1 (ApoA1) in the subject below that of a control subject receiving a placebo, a fixed 120 mg dose of ETC-1002, a fixed 180 mg dose of ETC-1002, or a fixed 2-80 mg dose for each one of one or more statins.

In some aspects, the method does not change the level of ApoA1 in the subject compared to that of a control subject receiving a placebo, a fixed 120 mg dose of ETC-1002, a fixed 180 mg dose of ETC-1002, or a fixed 2-80 mg dose for each one of one or more statins.

In some aspects, the method decreases the ratio of ApoB to ApoA1 in the subject above that of a control subject receiving a placebo, a fixed 120 mg dose of ETC-1002, a fixed 180 mg dose of ETC-1002, or a fixed 2-80 mg dose for each one of one or more statins.

In another aspect, the method decreases the number of drug-related AEs by at least 25%, by 35%, 45% or by 50% or more. In another aspect, the method decreases the number of muscle-related AEs by at least 50%, by 65%, 75% or by 85% or more.

In another aspect, methods disclosed herein significantly reduce the risk of a cardiovascular event in a subject. In some aspects this risk is reduced by up to 35% or more.

In some aspects, the methods herein provide for treating cardiovascular disease and/or reducing the risk of cardiovascular disease in a subject comprising administering an amount of a composition comprising ETC-1002 which is rapidly absorbed having a $T_{max}$ at less than 4 hours.

In some aspects, the methods herein provide for treating cardiovascular disease and/or reducing the risk of cardiovascular disease in a subject comprising administering an amount of a composition comprising ETC-1002 which do not prolong QTc or QT/QTc (TQT study). In one aspect, the add-on ETC-1002 therapy does not affect subject heart rate and PR and QRS intervals.

In some aspects, the methods herein provide for treating cardiovascular disease and/or reducing the risk of cardiovascular disease in a subject comprising administering an amount of a composition comprising ETC-1002 which systemic exposure, $AUC_{tau,ss}$, occurs with $t_{1/2}$ approximately 15 to 27 hours.

In some aspects, the methods herein provide for treating cardiovascular disease and/or reducing the risk of cardiovascular disease in a subject comprising administering an amount of a composition comprising ETC-1002 as add-on therapy to statin therapy which provides exposure measures AUC and/or $C_{max}$ indicating that the 2 regimens have no appreciable drug interaction. In one embodiment, neither the one or more statin(s) nor ETC-1002 exposure measures are outside safe values as established by confidence intervals.

In one aspect, the composition includes one or more statins as defined by the fixed dosages of atorvastatin (10 mg or 20 mg), simvastatin (5 mg, 10 mg, or 20 mg), rosuvastatin (5 mg or 10 mg), and/or pravastatin (10 mg, 20 mg, or 40 mg). In another aspect, the method includes one or more statins as defined by the fixed dosages of atorvastatin (10 mg or 20 mg), simvastatin (5 mg, 10 mg, or 20 mg), rosuvastatin (5 mg or 10 mg), and/or pravastatin (10 mg, 20 mg, or 40 mg). In yet another aspect, any combination of atorvastatin (10 mg or 20 mg), simvastatin (5 mg, 10 mg, or 20 mg), rosuvastatin (5 mg or 10 mg), and/or pravastatin (10 mg, 20 mg, or 40 mg) may be used in any embodiment or aspect disclosed herein.

In one aspect, the composition includes one or more statins as defined by the fixed dosages of Table 1 below:

TABLE 1

| High Intensity Statins | Moderate Intensity Statins | Low Intensity Statins |
| --- | --- | --- |
| Atorvastatin 40-80 mg | Atorvastatin 10-20 mg | Simvastatin 10 mg |
| Rosuvastatin 20-40 mg | Rosuvastatin 5-10 mg | Pravastatin 10-20 mg |
| Simvastatin 80 mg‡ | Simvastatin 20-40 mg | Lovastatin 20 mg |
|  | Pravastatin 40-80 mg | Fluvastatin 20-40 mg |
|  | Lovastatin 40 mg | Pitavastatin 1 mg |
|  | Fluvastatin XL 80 mg |  |
|  | Fluvastatin 40 mg twice daily |  |
|  | Pitavastatin 2-4 mg |  |

Compounds

Combinations of one or more statins and ETC-1002 are described herein. In one aspect, one or more or all of the statins are natural products isolated from a natural source such as Penecillium and *Aspergillus* fungi. In another aspect, one or more or all of the statins are synthetic, meaning they are made by advancing petrochemical starting material via organic synthesis to the desired statin compound.

Formula I below shows ETC-1002 and analogs of ETC-1002.

Formula I:

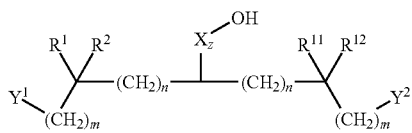

wherein (a) each occurrence of m is independently an integer ranging from 0 to 5; (b) each occurrence of n is independently an integer ranging from 3 to 7; (c) X is ($CH_2$), or Ph, wherein z is an integer from 0 to 4 and Ph is a 1,2-, 1,3-, or 1,4 substituted phenyl group; (d) each occurrence of $R^1$, $R^2$, $R^{11}$, and $R^{12}$ is independently H, ($C_1$-$C_6$)alkyl, ($C_2$-$C_6$)alkenyl, ($C_2$-$C_6$)alkynyl, phenyl, or benzyl, wherein $R^1$, $R^2$, $R^{11}$, and $R^{12}$ are not each simultaneously H; and (e) each occurrence of $Y^1$ and $Y^2$ is independently ($C_1$-$C_6$)alkyl, OH, COOH, $COOR^3$, $SO_3H$,

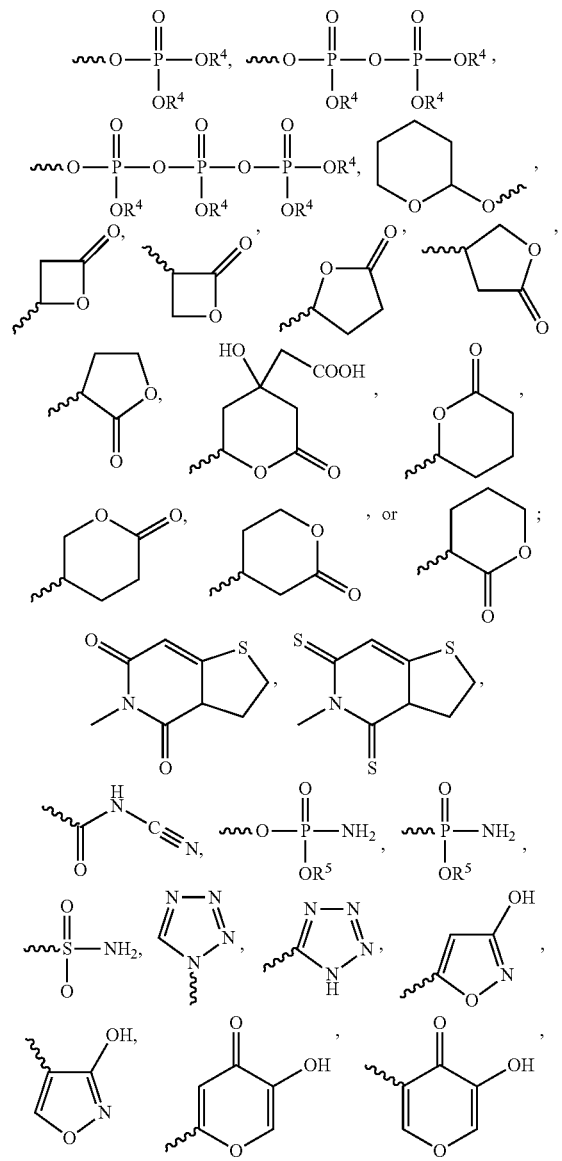

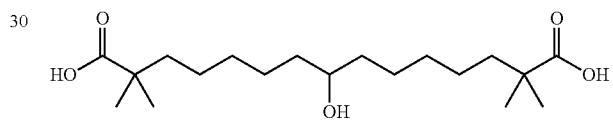

wherein: (i) $Y^1$ and $Y^2$ are not each simultaneously ($C_1$-$C_6$)alkyl; (ii) $R^3$ is ($C_1$-$C_6$)alkyl, ($C_2$-$C_6$)alkenyl, ($C_2$-$C_6$)alkynyl, phenyl, or benzyl and is unsubstituted or substituted with one or more halo, OH, ($C_1$-$C_6$)alkoxy, or phenyl groups, (iii) each occurrence of $R^4$ is independently H, ($C_1$-$C_6$)alkyl, ($C_2$-$C_6$)alkenyl, or ($C_2$-$C_6$)alkynyl and is unsubstituted or substituted with one or two halo, OH, $C_1$-$C_6$, alkoxy, or phenyl groups; and (iv) each occurrence of $R^5$ is independently H, ($C_1$-$C_6$)alkyl, ($C_2$-$C_6$)alkenyl, or ($C_2$-$C_6$)alkynyl.

Structure of ETC-1002:

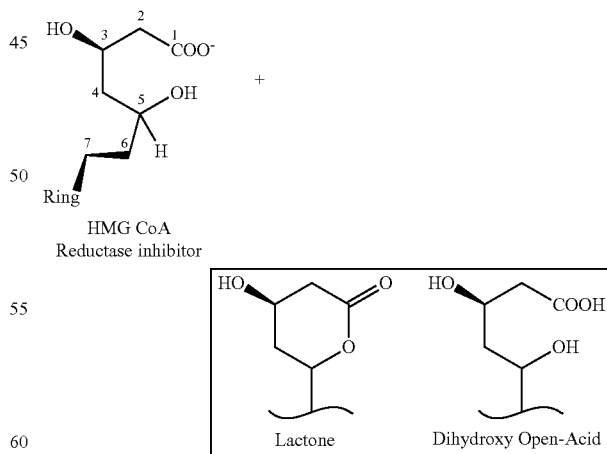

ETC-1002 can be referred to as 8-hydroxy-2,2,14,14 tetramethylpentadecanedioic acid.

Statin compounds inhibit HMGR enzymatic activity in the liver. In terms of structure, all statin compounds possess a dihydroxyheptanoic acid group or lactone thereof and a substituted ring system (shown below).

However, statins do differ with respect to the substituted ring structure. Some statins have a substituted decalin-ring structure while others have substituted aryl and heteroaryl ring systems. The structure of exemplary statin compounds is shown below, however, this list is in no way limiting.

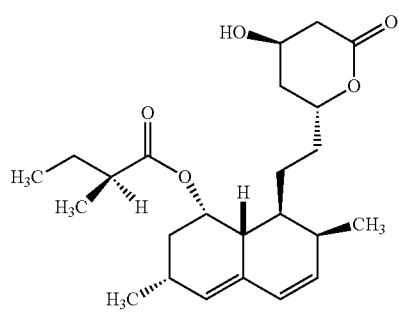
LOVASTATIN

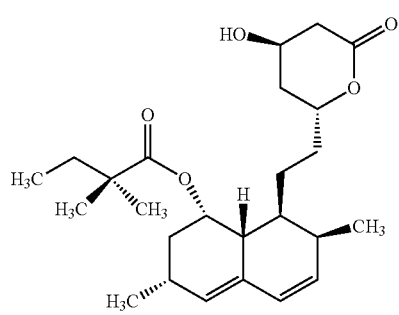
SIMVASTATIN

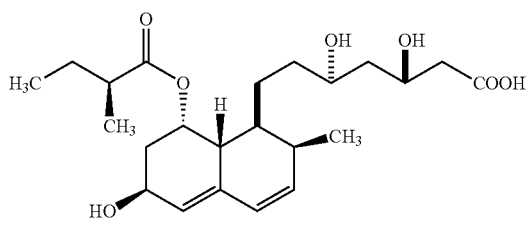
PRAVASTATIN

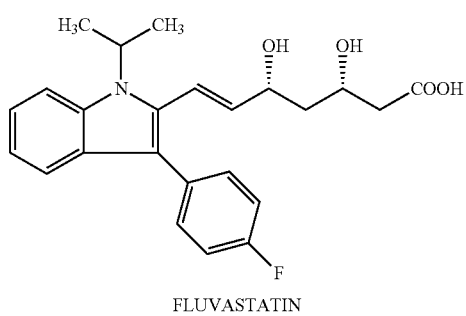
FLUVASTATIN

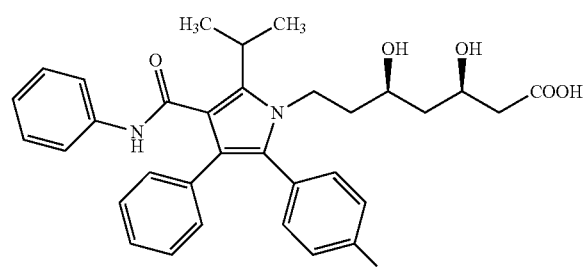
ATORVASTATIN

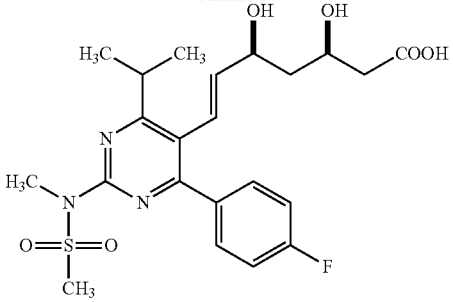
ROSUVASTATIN

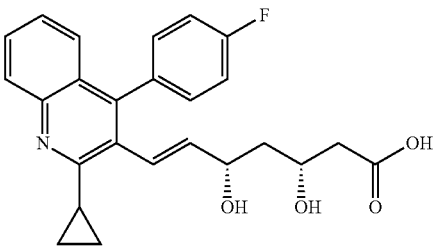
PITAVASTATIN

It is acknowledged that any and all analogs of ETC-1002 according to Formula I can be used in any of the methods and/or compositions or formulations disclosed herein. It is further acknowledged that any and all analogs of statins according to the description above can be used in any of the methods and/or compositions or formulations disclosed herein Synthesis of ETC-1002 and Statins ETC-1002 and the processes of the synthesis of ETC-1002 are disclosed in the issued U.S. Pat. No. 7,335,799. The details of this process can be found in the published U.S. patent publication No. US2005-0043278 A1, in paragraphs [0247]-103431 of the specification, each of which is herein incorporated by reference.

The synthesis of statins is known in the art. In a strategic and general disclosure, the synthesis of statins is disclosed in WO2005047276A2 which is herein incorporated by reference. Any other synthetic modifications for statins (or analogs of ETC-1002 for that matter), which may include unique or alternative ring systems, are within the purview of the skilled artisan. For example, the skilled artisan will be able to use synthetic reference texts to incorporate unique or desired substituted-aryl, heteroaryl, and decalin ring systems into the final statin compound. Such references include, but are not limited to: as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions. Volumes 1-40 (John Wiley, and Sons, 1991). March's Advanced Organic Chemistry, (John Wiley, and Sons, 5$^{th}$ Edition, 2001), and Larock's Comprehensive Organic Transformations (VCH Publishers Inc., 1989), T. W. Greene and P. G. M. Wuts. *Protecting Groups in Organic Synthesis*, Third Edition. Wiley, New York, 1999.

Methods of Use

The present invention provides methods for the treatment or prevention of a cardiovascular disease, comprising administering to a subject fixed doses of compounds or a composition comprising compounds of the invention and a pharmaceutically acceptable vehicle. As used herein, the term "cardiovascular diseases" refers to diseases of the heart and circulatory system. These diseases are often associated with dyslipoproteinemias and/or dyslipidemias. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarction; cerebral infarction and restenosis.

The present invention provides methods for the treatment or prevention of a dyslipidemia comprising administering to a subject fixed doses of compounds or a composition comprising compounds of the invention and a pharmaceutically acceptable vehicle. As used herein, the term "dyslipidemias" refers to disorders that lead to or are manifested by aberrant levels of circulating lipids. To the extent that levels of lipids in the blood are too high, the compositions of the invention are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org/cholesterol-/about_level.html and http://www.nhlbi.nih.gov/health/public/heart/chol/hb-c_what.html, respectively). At the present time, the recommended level of HDL cholesterol in the blood is above 35 mg/dL; the recommended level of LDL cholesterol in the blood is below 130 mg/dL; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating include but are not limited to hyperlipidemia and low blood levels of high density lipoprotein (HDL) cholesterol. In certain embodiments, the hyperlipidemia for prevention or treatment by the compounds of the present invention is familial hypercholesterolemia familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. .beta.-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, increasing the ratio of HDL to LDL in the blood of a patient, and inhibiting saponified and/or non-saponified fatty acid synthesis, said methods comprising administering to the patient a compound or a composition comprising a compound of the invention in an amount effective alter lipid metabolism.

Pharmaceutical Compositions

Methods for treatment of cardiovascular diseases are also encompassed by the present invention. Said methods of the invention include administering a therapeutically effective amount of one or more statins and ETC-1002. The fixed dose combination of one or more statins and ETC-1002 can be formulated in pharmaceutical compositions. These compositions comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, pill, powder or liquid form. A tablet or pill can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In one aspect, pharmaceutical compositions of the present invention are created from one or more of the compounds disclosed herein and are in the form of a pill.

In another aspect, herein provided is a method for lowering cholesterol or the associated markers disclosed herein (HDL-C, ApoA1, etc.) or for the treatment or prevention of a cardiovascular disease or dyslipoproteinemias and/or dyslipidemias, comprising administering to a subject a pharmaceutical composition in the form of a pill comprising ETC-1002 at a fixed dose of 120 mg or 180 mg and or a fixed dose from 2 to 80 mg dose of each one of one or more statins.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a small molecule or other pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

In one aspect the present disclosure provides for a method of treating cardiovascular disease or reducing the risk of cardiovascular disease in a subject, comprising administrating a fixed-dose combination of a fixed dose of ETC-1002 or an analog thereof and a fixed dose of one or more statins or an analog thereof to a subject in need thereof, optionally wherein ETC-1002 is administered at a fixed dose of 120 mg or at a fixed dose of 180 mg and each of the one more statins is administered at a fixed dose between 2-80 mg, and optionally wherein the method treats or reduces the risk of cardiovascular disease in the subject.

In one aspect the present disclosure provides for a method wherein the level of total cholesterol and non-HDL-C in the subject is below that of a control subject receiving placebo, a fixed 120 mg dose of ETC-1002, a fixed 180 mg dose of ETC-1002, or a fixed 2-80 mg dose for each one of one or more statins.

In one aspect the present disclosure provides for a method wherein the level of low density lipoprotein (LDL) in the subject is below that of a control subject receiving placebo, a fixed 120 mg dose of ETC-1002, a fixed 180 mg dose of ETC-1002, or a fixed 2-80 mg dose for each one of one or more statins.

In one aspect the present disclosure provides for a method wherein the number of LDL particles in the subject is below that of a control subject receiving placebo, a fixed 120 mg dose of ETC-1002, a fixed 180 mg dose of ETC-1002, or a fixed 2-80 mg dose for each one of one or more statins.

In one aspect the present disclosure provides for a method wherein the level of apolipoprotein B (ApoB) in the subject is less than that of a control subject receiving placebo, a fixed 120 mg dose of ETC-1002, a fixed 180 mg dose of ETC-1002, or a fixed 2-80 mg dose for each one of one or more statins.

In one aspect the present disclosure provides for a method wherein the level of apolipoprotein A-1 (ApoA1) in the subject is less than that of a control subject receiving placebo, a fixed 120 mg dose of ETC-1002, a fixed 180 mg dose of ETC-1002, or a fixed 2-80 mg dose for each one of one or more statins.

In one aspect the present disclosure provides for a method wherein the ratio of apolipoprotein B (ApoB) to apolipoprotein A-1 (ApoA1) in the subject is below that of a control subject receiving placebo, a fixed 120 mg dose of ETC-1002, a fixed 180 mg dose of ETC-1002, or a fixed 2-80 mg dose for each one of one or more statins.

In one aspect the present disclosure provides for a method wherein the subject has hypercholesterolemia.

In one aspect the present disclosure provides for a method wherein the subject is human.

In one aspect the present disclosure provides for a therapeutic composition of comprising a therapeutic amount of a fixed dose of ETC-1002 and a fixed dose for each one of one or more statins.

In one aspect the present disclosure provides for a composition wherein the amount is a 120 or 180 mg dose of ETC-1002 and a fixed 2-80 mg dose for each one of one or more statins.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3$^{rd}$ Ed. (Plenum Press) Vols A and B (1992).

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

It must be noted that, as used in the specification and the appended claims, the singular forms "a." "an" and "the" include plural referents unless the context clearly dictates otherwise.

Example 1

1. List of Abbreviations and Definitions of Terms

The following abbreviations and specialist terms are used in this study protocol.

TABLE 2

Abbreviations and Specialist Terms

| Abbreviation or Specialist Term | Explanation |
|---|---|
| ACL | Adenosine triphosphate-citrate lyase |
| ACS | Acyl-CoA synthetase |
| ADR | Adverse drug reaction |
| AE | Adverse event |
| ALB | Albumin |
| ALK-P | Alkaline phosphatase |
| ALT | Alanine aminotransferase |
| ANCOVA | Analysis of Covariance |
| apoA1 | Apolipoprotein A1 |
| apoB | Apolipoprotein B |
| aPTT | Activated partial thromboplastin time |
| ASCVD | Atherosclerotic cardiovascular disease |
| AST | Aspartate aminotransferase |
| ATP | Adenosine triphosphate |
| AUC | Area under the concentration-time curve |
| $AUC_{0-24}$ | Area under the curve during 24 hours |
| $AUC_{last}$ | Area under the plasma concentration-time profile from time zero to the time of the last quantifiable concentration |
| BLQ | Below the limit of quantification |
| BMI | Body mass index |
| BP | Blood pressure |
| BUN | Blood urea nitrogen |
| $C_{24}$ | Concentration in sample collected 24 hours post-dose, or prior to the next dose |
| Ca | Calcium |
| $C_{avg}$ | Average plasma concentration over the dosing interval |
| CFR | Code of Federal Regulations |
| CHD | Coronary heart disease |

TABLE 2-continued

Abbreviations and Specialist Terms

| Abbreviation or Specialist Term | Explanation |
|---|---|
| CI | Confidence interval |
| CK | Creatine kinase |
| Cl | Chloride |
| CL/F | Apparent oral clearance |
| $C_{max}$ | Observed maximum plasma concentration |
| $C_{min}$ | Minimum plasma concentration |
| CMV | Cytomegalovirus |
| CoA | Acetyl-coenzyme A |
| $CO_2$ | Carbon dioxide |
| CrCL | Creatinine clearance |
| CRF | Case report form |
| CT | Computed tomography |
| CYP | Cytochrome P450 |
| DBP | Diastolic blood pressure |
| ECG | Electrocardiogram |
| eCRF | Electronic case report form |
| EMA | European Medicines Agency |
| eGFR | Estimated glomerular filtration rate |
| EOS | End of study |
| FAS | Full analysis set |
| FDA | U.S. Food and Drug Administration |
| FPFV | First patient first visit |
| FSH | Follicle-stimulating hormone |
| GCP | Good Clinical Practice |
| GI | Gastrointestinal |
| $HbA_{1C}$ | Glycosylated hemoglobin, Type $A_{1C}$ |
| HBsAg | Hepatitis B surface antigen |
| Hct | Hematocrit |
| HCV | Hepatitis C virus |
| HDL-C | High-density lipoprotein cholesterol |
| HeFH | Heterozygous familial hypercholesterolemia |
| Hgb | Hemoglobin |
| HIV | Human immunodeficiency virus |
| HMG-CoA | 3-hydroxy-3-methylglutaryl coenzyme A |
| HR | Heart rate |
| hs-CRP | High-sensitivity C-reactive protein |
| IB | Investigator's Brochure |
| ICD | Informed Consent Document |
| ICH | International Conference on Harmonisation |
| IEC | Independent Ethics Committee |
| IMP | Investigational Medicinal Product |
| IND | Investigational New Drug Application |
| INR | International normalized ratio |
| IRB | Institutional Review Board |
| IUD | Intrauterine device |
| IWRS | Interactive web response system |
| IVRS | interactive voice response system |
| K | Potassium |
| LDH | Lactate dehydrogenase |
| LDL-C | Low-density lipoprotein cholesterol |
| LDLR | LDL receptor |
| LFT | Liver function test |
| LOCF | Last observation carried forward |
| LPLV | Last patient last visit |
| LSM | Least squares means |
| MCH | Mean corpuscular hemoglobin |
| MCHC | Mean corpuscular hemoglobin concentration |
| MCV | Mean corpuscular volume |
| MDRD | Modification of diet in renal disease |
| MedDRA | Medical Dictionary for Regulatory Activities |
| MED ID | Medication identification |
| mITT | Modified intent-to-treat |
| Na | Sodium |
| NLA | National Lipid Association |
| NOAEL | No-observed-adverse-effect level |
| non-HDL-C | Non-high-density lipoprotein cholesterol |
| OLA | Open-label atorvastatin |
| PCSK9 | Proprotein convertase subtilisin/kexin type 9 |
| PD | Pharmacodynamic |
| PE | Physical exam |
| PK | Pharmacokinetic(s) |
| PPAS | Per Protocol Analysis Set |
| PT | Prothrombin time |
| QD | Once daily |
| RBC | Red blood cell |
| SAE | Serious adverse event |
| SAP | Statistical Analysis Plan |
| SBP | Systolic blood pressure |
| SE | Standard error |
| SP | Safety population |
| $t_{1/2}$ | Terminal elimination half-live |
| T2DM | Type 2 diabetes mellitus |
| TB | Total bilirubin |
| TC | Total cholesterol |
| TEAE | Treatment-emergent adverse event |
| TG | Triglycerides |
| $t_{max}$ | Time of observed maximum plasma concentration |
| TSH | Thyroid-stimulating hormone |
| TQT | Thorough QT/QTc |
| ULN | Upper limit of normal |
| USA | United States of America |
| WBC | White blood cell |

Background on ETC-1002

Mechanism of Action

ETC-1002 is a small molecule inhibitor of adenosine triphosphate (ATP)-citrate lyase (ACL), an enzyme upstream of hydroxymethyl glutaryl coenzyme A (HMG-CoA) reductase (molecular target of statins) in the cholesterol biosynthesis pathway. ETC-1002 can mediate competitive inhibition of ACL. Inhibition of ACL decreases cholesterol synthesis in liver leading to increased LDLR expression and LDL particle clearance from the blood. Therefore, inhibition of ACL by ETC-1002 is via the same pathway as HMG-CoA reductase inhibition by statins.

An important differentiating feature of ETC-1002 is that, unlike statins, it does not inhibit cholesterol synthesis in skeletal muscle. Therefore, ETC-1002 is not expected to cause the adverse effects associated with inhibition of the cholesterol biosynthesis pathway in skeletal muscle.

Nonclinical Experience

The primary pharmacology of ETC-1002 was evaluated in several well-characterized and predictive rodent models of dyslipidemia. In these studies, ETC-1002 lowered LDL-C and triglycerides (TGs) and increased high-density lipoprotein cholesterol (HDL-C).

Results of the safety pharmacology studies did not identify any significant risks for patients over the range of exposures intended for clinical studies.

In toxicology studies, evaluations of ETC-1002 in mice, rats, and monkeys in oral studies up to 12 months in duration have been completed. No significant central nervous system, respiratory, or cardiovascular liabilities have been identified. Target organs identified in repeat-dose studies were liver and kidney in rats and monkeys, and changes were reversible following cessation of treatment. Changes in clinical laboratory parameters indicative of hepatic and renal function were observed in animals at doses lower than those associated with frank toxicity. Routine clinical laboratory parameters will continue to be monitored carefully in clinical trials.

ETC-1002 is non-mutagenic and non-clastogenic in both in-vitro and in-vivo genetic toxicology assays.

In the pivotal 6-month rat study, the no-observed-adverse-effect level (NOAEL) dose was 30 mg/kg/day in male and female rats and the corresponding area under the curve during 24 hours ($AUC_{0-24}$) values of the sum of ETC-1002 and ESP15228 were up to 528 μg·hr/mL. In the pivotal 12-month monkey study, the NOAEL dose was 60 mg/kg/ day and the corresponding $AUC_{0-24}$ value of the sum of ETC-1002 and ESP15228 was up to 4478 μg·hr/mL.

In vitro studies indicated that ETC-1002 is neither an inhibitor nor inducer of major cytochrome P450 (CYP) enzymes at clinically relevant plasma concentrations. In addition, ETC-1002 does not appear to inhibit major drug transporters.

Previous Human Experience

The entire clinical program for ETC-1002 (conducted between 2009 and 2015) has included approximately 1000 subjects and patients, with approximately 700 receiving ETC-1002 doses ranging from 2.5 up to 240 mg/day (multiple doses) for up to 12 weeks. There are 15 completed clinical studies (nine Phase 1 and six Phase 2), and integrated data summaries are based on the 6 completed Phase 2 studies.

An integrated analysis of six Phase 2 studies resulted in placebo-adjusted LS means for percent change from baseline of approximately 32% with ETC-1002 180 mg monotherapy, 50% with ETC-1002 180 mg+ezetimibe 10 mg, and 22% for 180 mg on top of stable statin therapy. Reduced LDL-C with ETC-1002 treatment was consistently accompanied by corresponding reductions in non-HDL-C, TC, LDL particle number and apoB. Notably, a pattern of hsCRP lowering across studies was also seen with a range of 20%-40% median change from baseline. The effect of ETC-1002 on HDL-C and TGs has been generally neutral.

PK data indicate that ETC-1002 is rapidly absorbed, with $T_{max}$ occurring at less than 4 hours for ETC-1002 and 7 hours for ESP15228. The $C_{max}$ of ETC-1002 and ESP15228 increase in proportion to increasing dose. However, systemic exposure, $AUC_{tau,ss}$, shows a slightly more than dose-proportional increase with increasing dose up to 120 mg daily and linear from 140 to 220 mg daily doses. Mean $t_{1/2}$ is approximately 15 to 27 hours. The metabolite, ESP15228, attains systemic exposure of 20%-40% of the parent, with the higher percentage observed at the lower doses; mean $t_{1/2}$ is slightly longer than that of the parent, with values of 20-33 hours.

No drug interaction was demonstrated with the combination of ETC-1002 and metformin or Ortho-Novum 1/35, a combined oral contraceptive. A food-effect/bioequivalence study demonstrated that ETC-1002 can be taken without regard to food.

The capsule and tablet formulations produce similar PK results.

The effect of ETC-1002 on the PK of atorvastatin was assessed in Study 1002-007. In this study, all patients received atorvastatin 10 mg/day during a 28-day run-in (statin stabilization) period followed by a treatment period during which patients received atorvastatin 10 mg/day plus a daily dose of ETC-1002 for 8 weeks. All patients started ETC-1002 at a dose of 60 mg/day, which was up-titrated every 2 weeks to 120 mg/day, then 180 mg/day, then 240 mg/day. For determination of a drug interaction between ETC-1002 and atorvastatin, the PK parameters of atorvastatin and ortho-hydroxy atorvastatin on Day 1 (at the end of the statin stabilization period; reference) were compared with corresponding PK parameters at Week 4 (at which time the ETC-1002 dose was 120 mg/day; Test 1) and Week 8 (at which time the ETC-1002 dose was 240 mg/day; Test 2). For atorvastatin and ortho-hydroxy atorvastatin, if the 90% confidence interval (CI) of the ratio of the exposure measures (AUC and/or $C_{max}$) fell between 80% and 125%, the 2 regimens would be considered similar with no drug interaction.

The results of the drug interaction evaluations show that a daily regimen of 10 mg atorvastatin plus 120 mg ETC-1002 provides an approximately 60% higher exposure to atorvastatin and ortho-hydroxy atorvastatin than daily doses of 10 mg atorvastatin alone. The higher dose of ETC-1002 (240 mg) administered with atorvastatin also gave higher exposure to the atorvastatin and ortho-hydroxy atorvastatin than administration of atorvastatin alone. The increases with 120 and 240 mg are similar with regard to AUC and $C_{max}$ increases for atorvastatin and metabolite. This study showed a transient increase in the exposure of atorvastatin (1.4× to 2.0×) when given in combination with ETC-1002. Importantly, ETC-1002 in combination with atorvastatin 10 mg was safe and well tolerated and resulted in incremental LDL-C lowering beyond atorvastatin alone.

The effect of steady-state ETC-1002 on the single-dose PK of simvastatin, pravastatin, and rosuvastatin was evaluated in Study 1002-012. In this study, healthy subjects were assigned to 1 of 3 statin cohorts and received a single oral dose of either simvastatin 20 mg (Cohort 1), pravastatin 40 mg (Cohort 2), or rosuvastatin 10 mg (Cohort 3) on the morning of Day −5. Serial PK blood samples were collected through the morning of Day −3. Starting on Day 1, all subjects received oral ETC-1002, 240 mg, once daily for 16 days. On the morning of Day 12, in addition to ETC-1002, subjects received a single dose of a statin drug, based on their cohort assignment; serial PK blood samples were collected.

The results of this study showed that plasma concentrations and PK parameters of ETC-1002 and its metabolite ESP15228 after the 12th daily 240-mg dose of ETC-1002 in combination with a single dose of simvastatin 20 mg, pravastatin 40 mg, or rosuvastatin 10 mg were consistent with those in previous monotherapy studies and a multiple-dose study of ETC-1002 in combination with atorvastatin.

Simvastatin and simvastatin exposure ($AUC_{0-inf}$) were increased by 29% and 91%, respectively, in the presence of steady-state ETC-1002 as compared to simvastatin alone. Simvastatin $C_{max}$ did not appear to be affected by co-administration with ETC-1002, whereas simvastatin $C_{max}$ was increased by 43% for simvastatin in combination with daily ETC-1002 relative to simvastatin alone. The magnitude of the observed geometric mean ratios for test (simvastatin with ETC-1002) to reference (simvastatin alone) AUC for the active metabolite simvastatin were consistent with a <2-fold increase; results showed that the magnitude of the interaction was lower for the prodrug parent compound (simvastatin).

Pravastatin exposure ($AUC_{inf}$ and $C_{max}$) was increased by 99% and ~2-fold, respectively, in the presence of steady-state ETC-1002 as compared to pravastatin alone. The magnitude of the observed geometric mean ratio for test (pravastatin with ETC-1002) to reference (pravastatin alone) AUC was consistent with a <2-fold increase.

Rosuvastatin exposure ($AUC_{inf}$ and $C_{max}$) was increased by 69% and 208%, respectively, in the presence of steady-state ETC-1002 as compared to rosuvastatin alone. The magnitude of the observed geometric mean ratio for test (rosuvastatin with ETC-1002) to reference (rosuvastatin alone) AUC was consistent with a <2-fold increase. As in Study 1002-007, the combination of ETC-1002 and statin therapy was safe and well tolerated.

The results of the thorough QT/QTc (TQT) study (1002-022) showed no significant change in QTc. Following daily ETC-1002 240 mg for 9 days, ETC-1002 does not prolong QT interval duration and has no clinically significant effect on heart rate and PR and QRS intervals.

In reviewing the incidence of TEAEs that occurred in ≥3 patients in any treatment group in the 6 integrated Phase 2 studies, there did not appear to be any dose-related trends in the frequency of TEAEs in the ETC-1002 treatment groups. The greatest number of patients experiencing at least 1 TEAE among ETC-1002-treated groups occurred in the ETC-1002 40-mg dose group (75.6%); this frequency was similar to the frequency of patients experiencing at least 1 TEAE in the placebo group (74.2%).

The system organ classes (SOCs) with the highest percentages of patients experiencing at least 1 TEAE in the ETC-1002 treatment groups were infections and infestations, and musculoskeletal and connective tissue disorders, and gastrointestinal disorders.

In the SOC of infections and infestations, the percent of patients experiencing at least 1 TEAE was highest in the ETC-1002 80 mg group (25.0%). Treatment groups involving ETC-1002 had a frequency of TEAEs in this SOC ranging from 11.6% to 25%, compared to ezetimibe 10 mg having 23.2%, baseline statins having 14.8%, and placebo having 11.8%. The most frequent TEAEs by preferred term in this SOC (those occurring in ≥3 patients in any treatment group) were bronchitis, nasopharyngitis, sinusitis, upper respiratory tract infection (URTI) and urinary tract infection (UTI). All TEAEs by preferred term in the SOC of infections and infestations occurred in ≤88% of patients in any treatment group.

In the SOC of musculoskeletal and connective tissue disorder, the percent of patients experiencing at least 1 TEAE in almost all ETC-1002 treatment groups was equal to or less than the frequency in the placebo group (23.7%), with the exception of the ETC-1002 240 mg group (32.4%). The most frequent TEAEs by preferred term in this SOC (ie, occurred in ≥3 patients in any treatment group) were arthralgia, back pain, muscle spasms, muscular weakness, myalgia, and pain in extremity. There were no dose-related trends in the frequency of myalgia in ETC-1002 treatment groups. The most frequent reports of myalgia were in the ETC-1002 120 mg+ezetimibe group (7.7%) and in the ezetimibe 10 mg group (6.1%). There were no reports of rhabdomyolysis. Almost all TEAEs by preferred term in the SOC of musculoskeletal and connective tissue disorder occurred in <8% of patients in any treatment group with the exception of arthralgia (9.7% of placebo group), back pain (8.1% of ezetimibe 10 mg group), and muscle spasms (13.5% of ETC-1002 240 mg group).

A total of 11 SAEs were reported in the 6 integrated Phase 2 studies; 5 (5/579; 0.9%) were in patients receiving ETC-1002, 1 (1/99; 1%) was a patient receiving ezetimibe 10 mg, 2 (2/61; 3.3%) were in patients receiving placebo+baseline statin, and 3 (3/93; 3.2%) were in patients receiving placebo alone. No SAE by preferred term had more than a single patient reporting the event. There were no muscle-related SAEs.

One patient died with cause unknown. A full narrative for this patient has been provided (18 Aug. 2014, SN-0083). The patient, a 55-year-old white male with hyperlipidemia and statin intolerance in the ETC-1002 120 mg treatment group (Study 1002-008), experienced sudden death on Study Day 98. He was found outside by a pool unresponsive and without a pulse. The death certificate did not provide a cause of death. The Investigator considered the event of sudden death (cause unknown) and possibly related to study drug since a temporal relationship could not be ruled out.

In general other measures of safety including laboratory results showed no clinically significant trends associated with ETC-1002 vs placebo or other comparator agents.

Dose Selection

Doses of ETC-1002 ranging from 40 to 240 mg/day have been evaluated in the Phase 2 program. Based on data from the integrated analysis of safety and efficacy, observed values and percent change from baseline in the primary efficacy endpoint. LDL-C together with a positive safety profile, support the choice of the 180-mg dose for the Phase 3 studies. An integrated analysis of six Phase 2 studies resulted in placebo-adjusted least squares means (LSM) for percent change from baseline of approximately 32% with ETC-1002 180 mg monotherapy, 50%6 with ETC-1002 180 mg+ezetimibe 10 mg, and 22% for 180 mg on top of stable statin therapy. The 180-mg dose was noted to have an excellent safety profile. Overall, balancing efficacy and safety the 180-mg dose was chosen for clinical development.

Background Therapy

ETC-1002 in this study is currently being evaluated as an add-on to high-dose statin (atorvastatin 80 mg) therapy.

Risk Benefit Summary

To date, the nonclinical and clinical data indicate that ETC-1002 has a favorable risk-benefit profile. The ability of ETC-1002 to achieve clinically meaningful LDL-C-lowering responses while demonstrating a favorable tolerability profile in a variety of patient populations supports continued development of ETC-1002, an oral ACL inhibitor.

Example 2

ETC-1002/High-Dose Statin Fixed Dose Combination

The LDL-C-lowering efficacy of ETC-1002 180 mg versus placebo when added to stable atorvastatin 80 mg background therapy for 28 days in statin-treated patients is evaluated.

Multiple-dose plasma PK of atorvastatin 80 mg and its active metabolites, ortho-hydroxy atorvastatin and para-hydroxy atorvastatin, alone and in combination with steady-state ETC-1002 180 mg is assessed.

The inventors contemplate that this add-on therapy is at least as effective as the previous studies and produces the same or better safety profile/tolerance.

Without wishing to be bound by theory the inventors believe that ETC-1002 180-mg tablets, when administered in addition to a stable high-dose statin (atorvastatin 80 mg), provides additional LDL-C lowering efficacy relative to atorvastatin alone and safe and is tolerated in statin-treated adult patients. ETC-1002 in combination will show increases in AUC and $C_{max}$ for statins (atorvastatin, rosuvastatin, pravastatin and simvastatin) up to 1.4-fold to 2.0-fold irrespective of structures, physico-chemical properties or doses for the statins and/or their metabolites when given.

Patients will be randomized in a ratio of 2:1 to receive treatments with either ETC-1002 180-mg tablet or matching placebo tablet in a double-blind fashion as add-on to statin therapy:

Patients will receive ETC-1002 as an add-on to high intensity statin therapy as shown in Table 3.

TABLE 3

Statin Dose Categories

| High Intensity Statins | Moderate Intensity Statins | Low Intensity Statins |
|---|---|---|
| Atorvastatin 40-80 mg | Atorvastatin 10-20 mg | Simvastatin 10 mg |
| Rosuvastatin 20-40 mg | Rosuvastatin 5-10 mg | Pravastatin 10-20 mg |

TABLE 3-continued

| Statin Dose Categories | | |
|---|---|---|
| High Intensity Statins | Moderate Intensity Statins | Low Intensity Statins |
| Simvastatin 80 mg‡ | Simvastatin 20-40 mg<br>Pravastatin 40-80 mg<br>Lovastatin 40 mg<br>Fluvastatin XL 80 mg<br>Fluvastatin 40 mg twice daily<br>Pitavastatin 2-4 mg | Lovastatin 20 mg<br>Fluvastatin 20-40 mg<br>Pitavastatin 1 mg |

Patients taking simvastatin 80 mg must have history of tolerating simvastatin 80 mg for a minimum of the last 12 months without any evidence of muscle toxicity.

Administration

Patients take the active tablet or placebo tablet orally once daily.

Patients will record dosing in diaries to record the time and date of each dose taken, whether they were fasted, and the time of a meal.

Pharmacokinetic Assessments

Whole blood samples to measure plasma concentrations of statin and active metabolites and ETC-1002 and active metabolites are collected.

Samples are collected and analyzed for basic fasting lipids including the calculated LDL-C, TC, HDL-C, non-HDL-C, TG, apoB, apoA1, and hsCRP.

TABLE 4

| Laboratory Parameters (Lipids) |
|---|
| Clinical Laboratory Test |
| Basic Lipid Parameters |
| Total cholesterol (TC)<br>Calculated low-density lipoprotein cholesterol (LDL-C)<br>Calculated non-HDL-C<br>High-density lipoprotein cholesterol (HDL-C)<br>Triglycerides (TG) |
| Other Parameters |
| High-sensitivity C-reactive protein (hs-CRP)<br>Apolipoprotein B (apoB)<br>Apolipoprotein A1 (apoA1) |

Assessment of Safety Parameters

Safety information includes the recordation of vital signs, AEs, concomitant medications, and ECG reports.

Vital Signs

Vital signs will include diastolic and systolic blood pressure as well as heart rate.

Electrocardiogram

Electrocardiogram collection occurs at designated sample collection points and is assessed using machine readings.

Adverse Events

An AE is any untoward medical occurrence when a patient is administered a pharmaceutical product, including control, and which does not necessarily have a causal relationship with treatment.

An AE can be any unfavorable and unintended sign (including an abnormal laboratory finding), symptom, or disease temporally associated with the use of a medicinal product, whether or not considered related to the medicinal product, any new disease or exacerbation of an existing disease, any deterioration in non-protocol-required measurements of laboratory value or other clinical test (eg, ECG or x-ray) that results in symptoms, a change in treatment, or discontinuation from study drug.

TEAEs are defined as AEs that begin or worsen after the first dose of IMP

Adverse Drug Reaction

All noxious and unintended responses to a medicinal product related to any dose should be considered an adverse drug reaction (ADR). "Responses" to a medicinal product means that a causal relationship between a medicinal product and an AE is at least a reasonable possibility (ie, the relationship cannot be ruled out).

An unexpected ADR is defined as an adverse reaction, the nature or severity of which is not consistent with the applicable product information (eg. IB for an unapproved investigational product or package insert/summary of product characteristics for an approved product).

The severity of the AE is characterized as mild, moderate, or severe according to the following definitions:

Mild: Events are usually transient and do not interfere with the patient's daily activities Moderate: Events introduce a low level of inconvenience or concern to the patient and may interfere with daily activities Severe: Events interrupt the patient's usual daily activity, are incapacitating with inability to do usual activities, or significantly affect clinical status and warrant intervention and/or close follow-up Note: A severe AE need not be serious and an SAE need not, by definition, be severe.

Definition of Serious Adverse Event

An SAE is defined as any AE occurring at any dose that results in any of the following outcomes:

Results in death

Is life-threatening

Requires in-patient hospitalization or prolongation of existing hospitalization

Results in persistent or significant disability/incapacity, or substantial disruption of the ability to conduct normal life functions Is a congenital anomaly/birth defect An important medical event Important medical events that may not result in death, be life threatening, or require hospitalization may be considered an SAE when, based upon appropriate medical judgment, they may jeopardize the patient and may require medical or surgical intervention to prevent one of the outcomes listed in this definition. Examples of such medical events include allergic bronchospasm requiring intensive treatment in an emergency room, blood dyscrasias, convulsions that do not result in inpatient hospitalization, or the development of drug dependency or drug abuse.

Determination of Sample Size

For the LDL C-lowering study objective, the sample size of 40 patients in the atorvastatin 80 mg/day+ETC 1002 treatment group and 20 patients in the atorvastatin 80 mg/day+placebo group (60 patients overall) is expected to provide 80% power to detect a difference of 15% in the percent change from baseline to Day 29 in calculated LDL C between atorvastatin 80 mg/day+ETC 1002 and atorvastatin 80 mg/day+placebo. This calculation is based on a 2 sided t test at the 5% level of significance, a common standard deviation of 18% and a dropout rate of 10%. Sample-size calculations were performed using nQuery Advisor®, version 7.0 (Statistical Solutions).

For the PK drug interaction study objective, the sample size of 36 patients in the atorvastatin 80 mg/day+ETC 1002 treatment group (assuming data from 4 patients will not be included) is expected to provide 79% or greater power for each parameter/analyte, if the expected Test/Reference ratio of exposure measures is 100% (no difference between atorvastatin alone and atorvastatin+ETC 1002) and the acceptance criterion is 80% to 125% for the 90% confidence interval (CI). Thus, 36 patients planned in 1002 035 is anticipated to adequately characterize the effect of ETC 1002 on atorvastatin PK.

The Per Protocol Analysis Set (PPAS) is defined as the set of patients in the FAS who additionally have all pre-dose PK samples >BLQ (for placebo patients, it is pre-dose atorvastatin PK samples >BLQ; for ETC 1002 patients, it is pre-dose atorvastatin and pre-dose ETC samples >BLQ) and have Day 29 lipid assessments. The PPAS will be used for select sensitivity analyses of the lipid parameters.

Pharmacodynamic Analysis

Summarization of lipids (LDL-C, TC, HDL-C, non-HDL-C, TG, apoB, apoA1 and hsCRP) over time will be provided. For each parameter, the summary will include the value and the percent change from baseline (for post-baseline time points) in the value.

The percent change from baseline is calculated for LDL-C and the other parameters.

Pharmacokinetic and Drug Interaction Analysis

Pharmacokinetic parameters for atorvastatin, ortho-hydroxy atorvastatin, para-hydroxy atorvastatin, ETC 1002, and ESP15228 following multiple-dose administration are derived from the plasma concentration-time profiles as follows:

Cmax: Maximum observed plasma concentration tmax: Time for Cmax, as observed at the time of first occurrence within the profile AUClast: Area under the plasma concentration-time profile from time zero to the time of the last quantifiable concentration (Clast), calculated using the Linear/Log trapezoidal method AUC24: Area under the plasma concentration-time profile from time zero to 24 hours, calculated using the Linear/Log trapezoidal method CL/F: Apparent oral clearance, calculated from Dose/AUC24, for atorvastatin and ETC 1002 only Cmin: Minimum plasma concentration, as observed prior to drug administration Cavg: Average plasma concentration, calculated from AUC24 divided by the dosing interval, 24 hours C24: Concentration in sample collected 24 hours post-dose, or prior to the next dose Standard noncompartmental PK analysis will be used to calculate Cmax, tmax, AUClast, AUC24, Cmin, Cavg, and C24. Pharmacokinetic parameters will be summarized with descriptive statistics by sampling day, and dose of ETC 1002 using the PK parameter population. A different PK parameter population may be used for each analyte.

Drug Interaction Evaluation from PK Analyses

Safety Assessments

Safety assessments include AEs, clinical safety laboratories, PEs, vital signs, and ECGs.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed:

1. A fixed-dose composition comprising ETC-1002 and one or more statins selected from the group consisting of rosuvastatin and atorvastatin, wherein
   the fixed dose of ETC-1002 is 180 mg,
   the fixed dose of rosuvastatin is 20-40 mg,
   the fixed dose of atorvastatin is 40-80 mg, and
   administration of the fixed-dose composition results in an equal or decreased frequency of myalgia compared to the administration of the fixed dose of the one or more statins.

* * * * *